US012616562B2

(12) United States Patent (10) Patent No.: US 12,616,562 B2

Shaker et al. (45) Date of Patent: May 5, 2026

(54) SYSTEMS AND METHODS FOR CONTINENCE TRAINING

(71) Applicants:The Medical College of Wisconsin, Inc., Milwaukee, WI (US); University of Southern California, Los Angeles, CA (US)

(72) Inventors: Reza Shaker, Brookfield, WI (US); Anisa Shaker, Los Angeles, CA (US)

(73) Assignees: The Medical College of Wisconsin, Inc., Milwaukee, WI (US); University of Southern California, Los Angeles, CA (US)

( * ) Notice: Subject to any disclaimer, the term of this patent is extended or adjusted under 35 U.S.C. 154(b) by 1008 days.

(21) Appl. No.: 17/425,434

(22) PCT Filed: Jan. 23, 2020

(86) PCT No.: PCT/US2020/014820

§ 371 (c)(1),
(2) Date: Jul. 23, 2021

(87) PCT Pub. No.: WO2020/154521

PCT Pub. Date: Jul. 30, 2020

(65) Prior Publication Data

US 2022/0087806 A1 Mar. 24, 2022

Related U.S. Application Data

(60) Provisional application No. 62/795,719, filed on Jan. 23, 2019.

(51) Int. Cl.
*A61F 2/00* (2006.01)
*A63B 23/20* (2006.01)
(Continued)

(52) U.S. Cl.
CPC ............ *A61F 2/0027* (2013.01); *A63B 23/20* (2013.01); *A61M 2025/0002* (2013.01);
(Continued)

(58) Field of Classification Search
None
See application file for complete search history.

(56) References Cited

U.S. PATENT DOCUMENTS 2,919,135 A * 12/1959 Marchionda ........... A63H 33/00
273/119 B
3,646,929 A * 3/1972 Bonnar ................... A61F 2/005
606/119

(Continued)

FOREIGN PATENT DOCUMENTS

DE 4436796 4/1996
GB 1532360 A * 11/1978 ............. A61B 5/227
(Continued)

OTHER PUBLICATIONS

Stacy B. Menees et al., "Prevalence of and Factors Associated With Fecal Incontinence: Results From a Population-Based Survey", Gastroenterology, vol. 154, issue 6, pp. 1672-1681, May 2018.
(Continued)

*Primary Examiner* — Shila Jalalzadeh Abyaneh
(74) *Attorney, Agent, or Firm* — Quarles & Brady LLP

(57) ABSTRACT

A medical device for reducing incontinence can be dimensioned to be placed in an interior region of a subject surrounded by muscle tissue. The medical device can include a first balloon having an interior space containing a fluid. The proximal end of a first fluid conduit can be coupled to an outlet of the first balloon. The medical device can also include a pressure sensing detector coupled to a distal end of the first fluid conduit. The pressure sensing detector can include a second balloon. The second balloon
(Continued)

can also be in fluid communication with the interior space of the first balloon. The first balloon can be compressed from the contraction of the muscle tissue, which can displace a portion of the fluid within the interior space of the first balloon. The portion of fluid moves towards the second balloon and causes the second balloon to increase in interior volume thereby indicating a contraction force of the muscle tissue.

8 Claims, 13 Drawing Sheets

(51) Int. Cl.
    *A61M 25/00* (2006.01)
    *A61M 25/10* (2013.01)
(52) U.S. Cl.
    CPC .................. *A61M 25/10186* (2013.11); *A61M 2210/1475* (2013.01); *A63B 2214/00* (2020.08)

(56) References Cited

U.S. PATENT DOCUMENTS

| | | | | |
|---|---|---|---|---|
| 3,658,326 | A | * | 4/1972 | Fawick .................. A63B 23/16 482/49 |
| 3,726,273 | A | * | 4/1973 | Cole ...................... A61B 5/227 600/38 |
| 4,167,938 | A | * | 9/1979 | Remih ................... A63B 23/20 606/191 |
| 4,530,496 | A | * | 7/1985 | Smith ................ A63B 21/0085 482/909 |
| 5,090,424 | A | * | 2/1992 | Simon ................... A61F 2/0013 128/885 |
| 5,674,238 | A | | 10/1997 | Sample et al. |
| 6,063,045 | A | | 5/2000 | Wax et al. |
| 6,843,766 | B1 | | 1/2005 | Nemir et al. |
| 6,918,862 | B1 | * | 7/2005 | Comeau ................. A63B 23/16 482/44 |
| 8,369,953 | B2 | | 2/2013 | Peddicord |
| 10,945,652 | B1 | * | 3/2021 | Wanderman ........... A61B 5/227 |
| 11,027,120 | B2 | | 6/2021 | Peddicord |
| 2001/0053920 | A1 | * | 12/2001 | Shaker ................. A61B 5/4233 606/197 |
| 2003/0087734 | A1 | * | 5/2003 | Kring ..................... A63B 23/20 482/112 |
| 2005/0277805 | A1 | | 12/2005 | Hatton |
| 2006/0229174 | A1 | * | 10/2006 | Bonutti .............. A63B 23/1281 482/44 |
| 2012/0330132 | A1 | * | 12/2012 | Sorajja .............. A61M 25/0105 600/420 |
| 2014/0243584 | A1 | * | 8/2014 | Bercovich ............... A61F 2/005 600/29 |
| 2016/0029944 | A1 | * | 2/2016 | Galliano ............. B41J 2/14072 600/587 |
| 2017/0135846 | A1 | | 5/2017 | Weiss et al. |
| 2018/0132991 | A1 | * | 5/2018 | Bercovich ............... A61F 2/005 |
| 2018/0344250 | A1 | * | 12/2018 | McKinney ........... A61B 5/6853 |

FOREIGN PATENT DOCUMENTS

| | | | | | |
|---|---|---|---|---|---|
| GB | | 2444034 | A | * | 5/2008 ............. A61H 19/34 |
| JP | | H01-178003 | U | | 12/1989 |
| JP | | H10-314339 | A | | 12/1998 |
| KR | | 10-1713934 | | | 3/2017 |
| WO | | 99/28002 | A1 | | 6/1999 |

OTHER PUBLICATIONS

Coss-Adame, et al., "Accuracy and Reproducibility of High-definition Anorectal Manometry and Pressure Topography Analyses in Healthy Subjects", Clin Gastroenterol Hepatol. Jun. 2015; 13(6): 1143-1150.
PCT/US2020/041820—International Search Report and Written Opinion—Jun. 22, 2022, 13 pages.
EP20745691.4—Supplementary European Search Report—Sep. 27, 2022.
Machine Translation of JP H10-314339.
Machine Translation of JP H01-178003.
Machine Translation of KR 10-1713934.
Machine Translation of DE 4436796.
Cerulli et al., Progress in Biofeedback Conditioning for Fecal Incontinence, Gastroenterology 76:742-746, 1979.
Schuster et al., Simultaneous Manometric Recording Of Internal And External Anal Sphincteric Reflexes, Bulletin Of The Johns Hopkins Hospital, vol. 116, 1965, pp. 79-88.

* cited by examiner

SYSTEMS AND METHODS FOR CONTINENCE TRAINING

CROSS-REFERENCE TO RELATED APPLICATIONS

This application represents the national stage entry of PCT/US2020/014820 filed on Jan. 23, 2020 and claims priority to U.S. Patent Application No. 62/795,719 filed Jan. 23, 2019, which is hereby incorporated by reference herein in its entirety for all purposes.

STATEMENT REGARDING FEDERALLY SPONSORED RESEARCH

Not applicable.

BACKGROUND

Fecal incontinence is an overarching term or symptom defined by the decrease in ability to control (or contain) bowel movements. In some cases, the decreased control can cause feces to uncontrollably leak from the individual's rectum, which can cause significant social anxiety and decreased quality of life. Fecal incontinence tends to be especially prevalent among older individuals (the older adult population), however, the condition may be difficult to treat, as patients generally do not present incontinence symptoms to physicians (e.g., due to embarrassment over the symptoms). Correspondingly, physicians often fail to ask directly about incontinence symptoms, because of the stigma associated with this condition.

Fecal incontinence not only affects individuals across the globe, but also a significant portion of people within the U.S. For example, a national survey of 7200 individuals showed one in seven individuals reporting any history of fecal incontinence and one in three reporting fecal incontinence within the preceding week. See, Stacy B. Meness et al., "Prevalence of and Factors Associated With Fecal Incontinence: Results From a Population-Based Survey", *Gastroenterology, vol.* 154, issue 6, pages 1672-1681, May 2018. The incidence of fecal incontinence also increases with an increasing age of the population. For example, the highest prevalence of fecal incontinence is in individuals over age 65. Additionally, according to another survey of around 70,000 individuals, 14.4% of the respondents (10,033 individuals) reported a history of fecal incontinence, and 33.3% of the respondents (~23,224 individuals) had experienced at least one episode of fecal incontinence in the week prior to the survey. Additionally, the third of individuals with fecal incontinence experienced a week prior to the survey, said it interfered with their daily activities. Id. "Increasing age and concomitant diarrhea and constipation were associated with increased odds [of] fecal incontinence". Id. As indicated above, fecal incontinence generally increases with an individual's age. For example, compared to individuals aged 18-24 years, the odds of having ever experienced fecal incontinence rose by 29% among those aged 25-45 years, rose by 72% among those aged 45-64 years, and rose by 118% among persons aged 65 years and older. Id.

Current therapy for fecal incontinence is very limited. Surgical approaches exist but have not been successful. Thus, it would be desirable to have improved systems and methods for reducing fecal incontinence.

SUMMARY OF THE INVENTION

Some embodiments of the disclosure provide a medical device for reducing incontinence. The medical device can be dimensioned in order to be placed in an interior region of a subject surrounded by muscle tissue. The medical device can include a first balloon having a first end, a second end, an interior surface, and an exterior surface. The interior surface can define an interior space, where the interior space includes a fluid. The first balloon can have an outlet disposed on the first end of the balloon, where the outlet can be in fluid communication with the interior space of the first balloon. The medical device can also include a first fluid conduit having a proximal end and a distal end. The proximal end can be coupled to the outlet of the first balloon, where the fluid conduit can be in fluid communication with the outlet and the interior space of the first balloon. The medical device can also include a pressure sensing detector coupled to the distal end of the first fluid conduit. The pressure sensing detector can include a second balloon. The second balloon can also be in fluid communication with the interior space of the first balloon. The first balloon can be compressed from the contraction of the muscle tissue, which can displace a portion of the fluid within the interior space of the first balloon. The portion of fluid moves towards the second balloon and causes the second balloon to increase in interior volume thereby indicating a contraction force of the muscle tissue.

In some embodiments, the interior region includes a transsphincteric region.

In some embodiments, the interior region includes a vaginal cavity.

In some embodiments, the medical device further comprises: a second fluid conduit in fluid communication with the interior space of the first balloon and a source of fluid, wherein the second fluid conduit defines a fluid path, and wherein the source of fluid supplies the fluid; and a valve positioned in the fluid path, wherein the valve allows the fluid from the fluid source to flow into the interior space of the first balloon thereby expanding the first balloon.

In some embodiments, the valve allows the fluid within the interior space of the first balloon to flow out of the interior space of the first balloon.

In some embodiments, the valve releases the fluid within the interior space of the first balloon into the atmosphere.

In some embodiments, the fluid within the interior space of the first balloon defines a maximum amount of fluid.

In some embodiments, the amount of fluid within the interior space of the first balloon cannot exceed the maximum amount of fluid.

In some embodiments, the maximum amount of fluid within the interior space of the first balloon defines a first loading pressure.

In some embodiments, the first loading pressure compresses the muscle tissue.

Some embodiments of the disclosure provide a medical device for reducing incontinence. The medical device can be dimensioned to be placed in an interior region of a subject surrounded by muscle tissue. The medical device can include a fluid enclosure having a first end and a second end, where the fluid enclosure defines an interior space. The fluid enclosure can be capable of expelling and receiving a fluid, and the fluid enclosure can have an inlet. The medical device can also include a first fluid conduit coupled to the inlet of the fluid enclosure, where the first fluid conduit can define a fluid path. The fluid path can be in fluid communication with the interior space of the fluid enclosure. The medical device can also include a valve positioned in the fluid path. The medical device can also include a source of fluid in fluid communication with the fluid path. The medical device can also include a pressure sensor in fluid communication with the interior space of the fluid enclosure. The medical device can also include a controller in electrical communication with the valve and the pressure sensor, where the controller is configured to execute a program stored in the controller to: open the valve, such that fluid from the source of fluid flows into the interior space the fluid enclosure thereby expanding the fluid enclosure to a first loading pressure, close the valve, once the pressure sensor senses the first loading pressure, thereby preventing further influx of fluid into the fluid enclosure, sense a first compression pressure when the fluid enclosure is compressed, open the valve, such that fluid from the source of fluid flows into the interior space the fluid enclosure thereby expanding the fluid enclosure to a second loading pressure, close the valve, once the pressure sensor senses the second loading pressure, thereby preventing further influx of fluid into the fluid enclosure, and sense a second compression pressure when the fluid enclosure is compressed. The second loading pressure can be greater than the first loading pressure. After the subject completes a specific regiment (e.g., a first regiment) for a specific duration (e.g., two weeks) the medical device can increase the amount of fluid or the pressure within the fluid enclosure. This increases the loading pressure/force on the transsphincteric muscles, and once a new regiment is completed (e.g., a second regiment), the transsphincteric muscles become even stronger when compared to the transsphincteric muscles after the first regiment.

Some embodiments of the disclosure provide a method for reducing incontinence. The method can include placing a first fluid enclosure into an interior region of a subject, the first fluid enclosure having a first interior surface, the first interior surface defining a first interior space, the interior region of the subject including muscle tissue, the first fluid enclosure being dimensioned to provide a first force opposite in direction to a contracting force of the muscle tissue. The method can also include contracting the muscle tissue thereby compressing the first fluid enclosure and displacing a portion of the fluid within the first fluid enclosure. The method can also include repeating the contraction of the muscle a plurality of times, such that the muscle tissue strengthens.

In some embodiments, the plurality of times is thirty times.

In some embodiments, the plurality of times is thirty times, twice per day.

In some embodiments, the method further comprises: placing a second fluid enclosure into the interior region of the subject, the second fluid enclosure having a second interior surface, the second interior surface defining a second interior space, the second fluid enclosure being dimensioned to provide a second force opposite in direction to a contracting force of the muscle tissue.

In some embodiments, the second force is greater than the first force.

In some embodiments, the method further comprises contracting the muscle tissue thereby compressing the second fluid enclosure and displacing a portion of the fluid within the second fluid enclosure.

In some embodiments, the method further comprises repeating contracting the muscle tissue thereby compressing the second fluid enclosure and displacing a portion of the fluid within the second fluid enclosure, a number of times, such that the muscle tissue strengthens defining a second muscle strength.

In some embodiments, the second muscle strength is greater than the first muscle strength.

In some embodiments, the number of times is in a range of ten to fifty times.

In some embodiments, the number of times is in a range of ten to fifty times, twice per day.

In some embodiments, the first fluid enclosure has a first rigidity, and the second fluid enclosure has a second rigidity.

In some embodiments, the second rigidity is greater than the first rigidity.

Some embodiments of the disclosure provide a kit for reducing incontinence in a subject. The kit includes a first balloon having a first end and a second end, the balloon defining an interior surface and an exterior surface, the interior surface defining a first interior space, the first interior space including a fluid, the first balloon having an outlet disposed on the first end of the balloon, the outlet being in fluid communication with the interior space of the first balloon, the first balloon having a first loading pressure; a second balloon having a first end and a second end, the second balloon defining a second interior surface and a second exterior surface, the second interior surface defining a second interior space, the second interior space including a fluid, the second balloon having a second outlet disposed on the first end of the second balloon, the second outlet being in fluid communication with the second interior space of the second balloon, the second balloon having a second loading pressure; a fluid conduit defining a proximal end and a distal end, the proximal end being structured to be removably coupled to the first outlet such that the fluid conduit is in fluid communication with the first interior space of the first balloon, the proximal end being structured to be removably coupled to the second outlet such that the fluid conduit is in fluid communication with the second interior space of the second balloon; and a pressure sensing detector structured to be coupled to the distal end of the fluid conduit; wherein the second loading pressure is greater than the first loading pressure.

BRIEF DESCRIPTION OF THE DRAWINGS

The invention will be better understood and features, aspects and advantages other than those set forth above will become apparent when consideration is given to the following detailed description and claims. Such detailed description makes reference to the following drawings.

5

Figure 10:
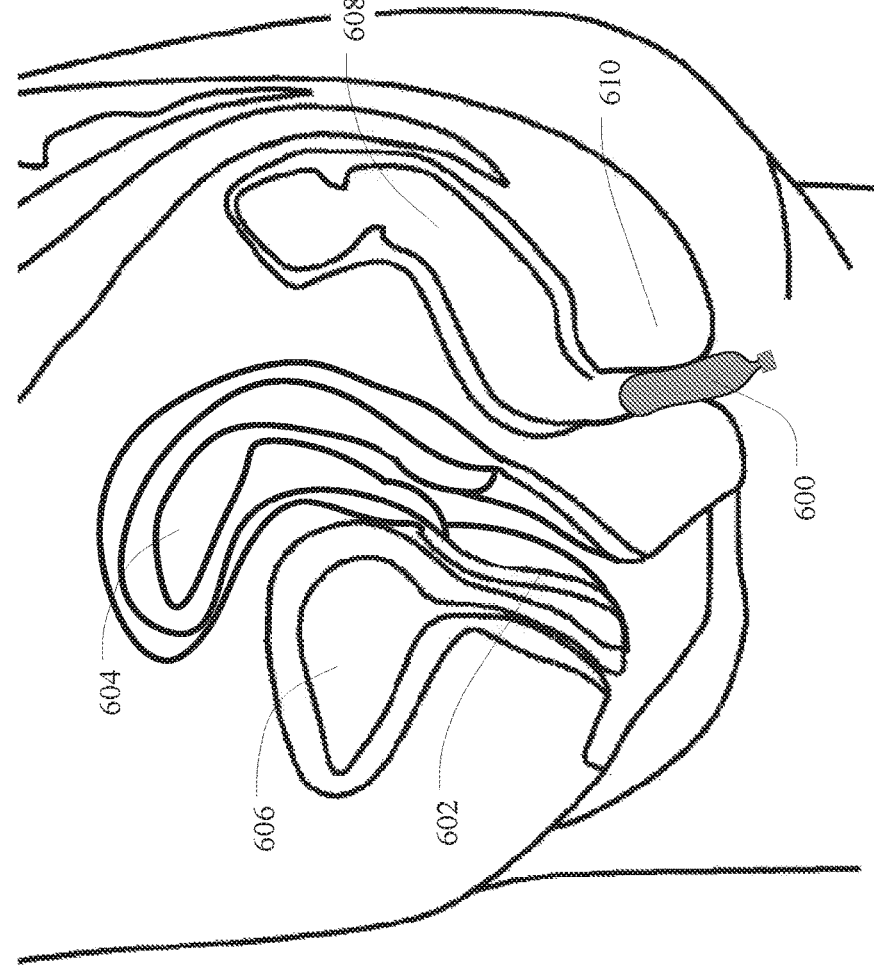
FIG. 10 is a transsphincteric sagittal view of a placement of a transsphincteric system.
Figure 12:
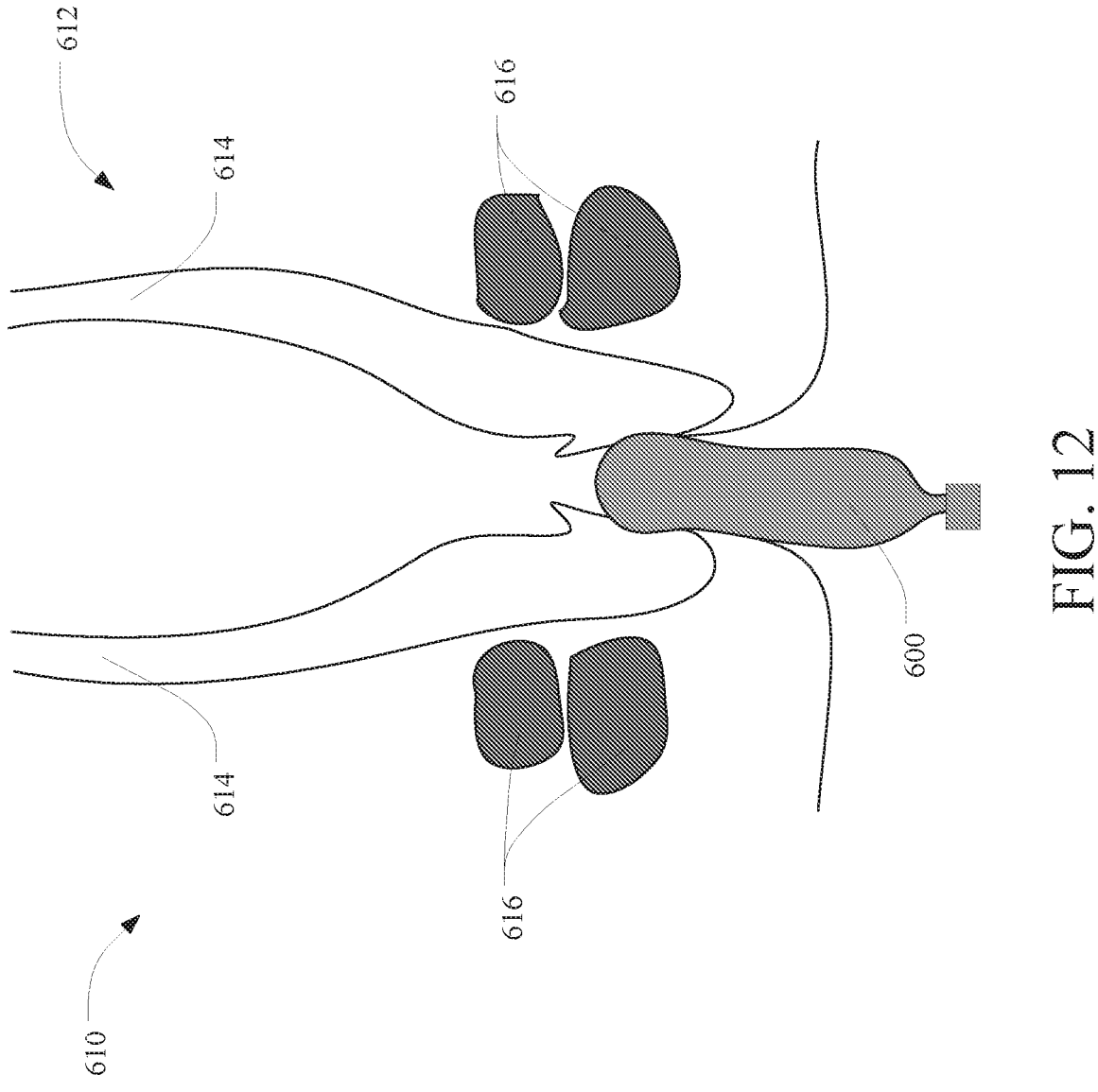

FIG. 12 is a transsphincteric coronal cross-sectional view of the transsphincteric system of FIG. 10.

Figure 13:
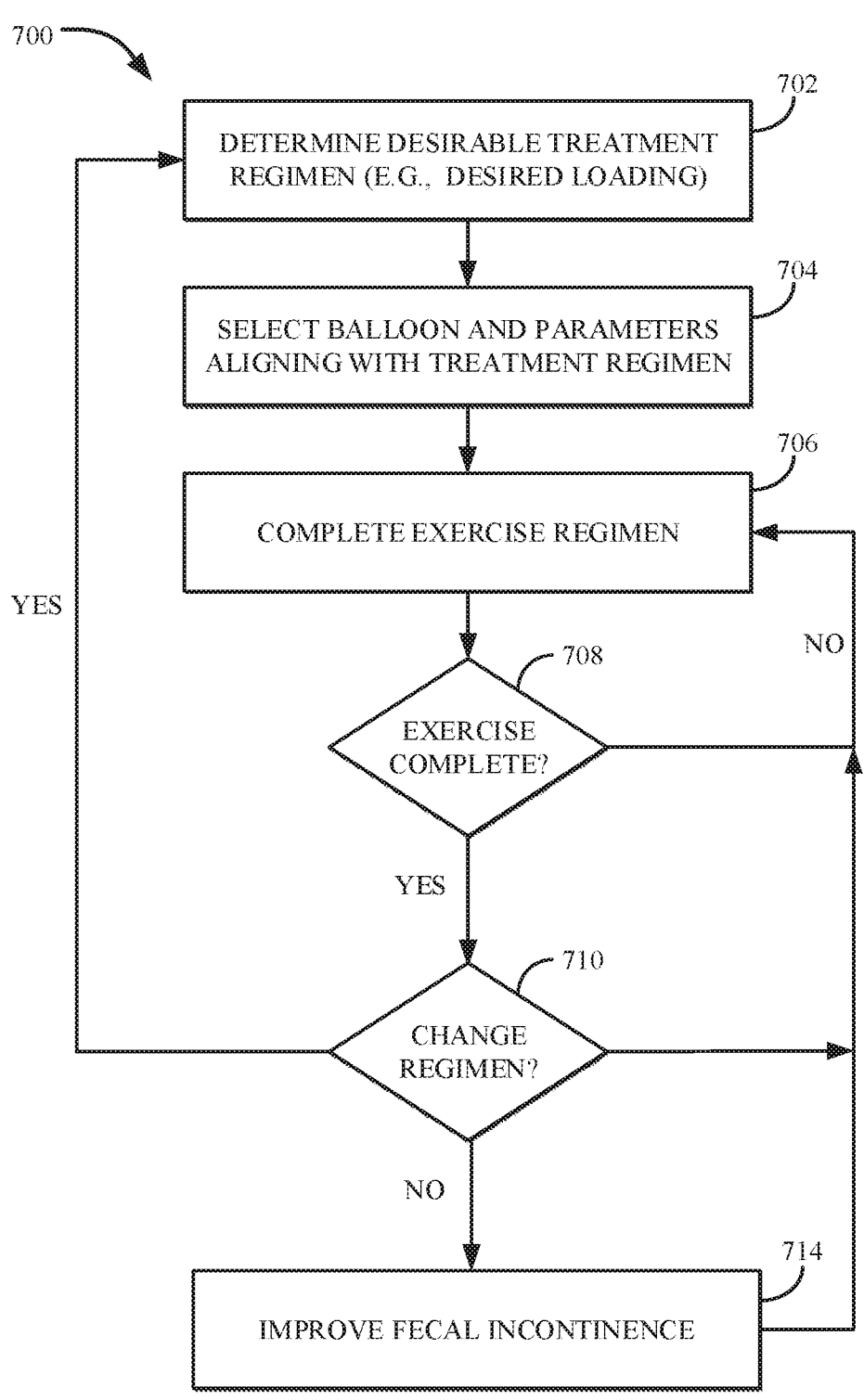

FIG. 13 is a flowchart of a process for reducing fecal incontinence.

Figure 14:
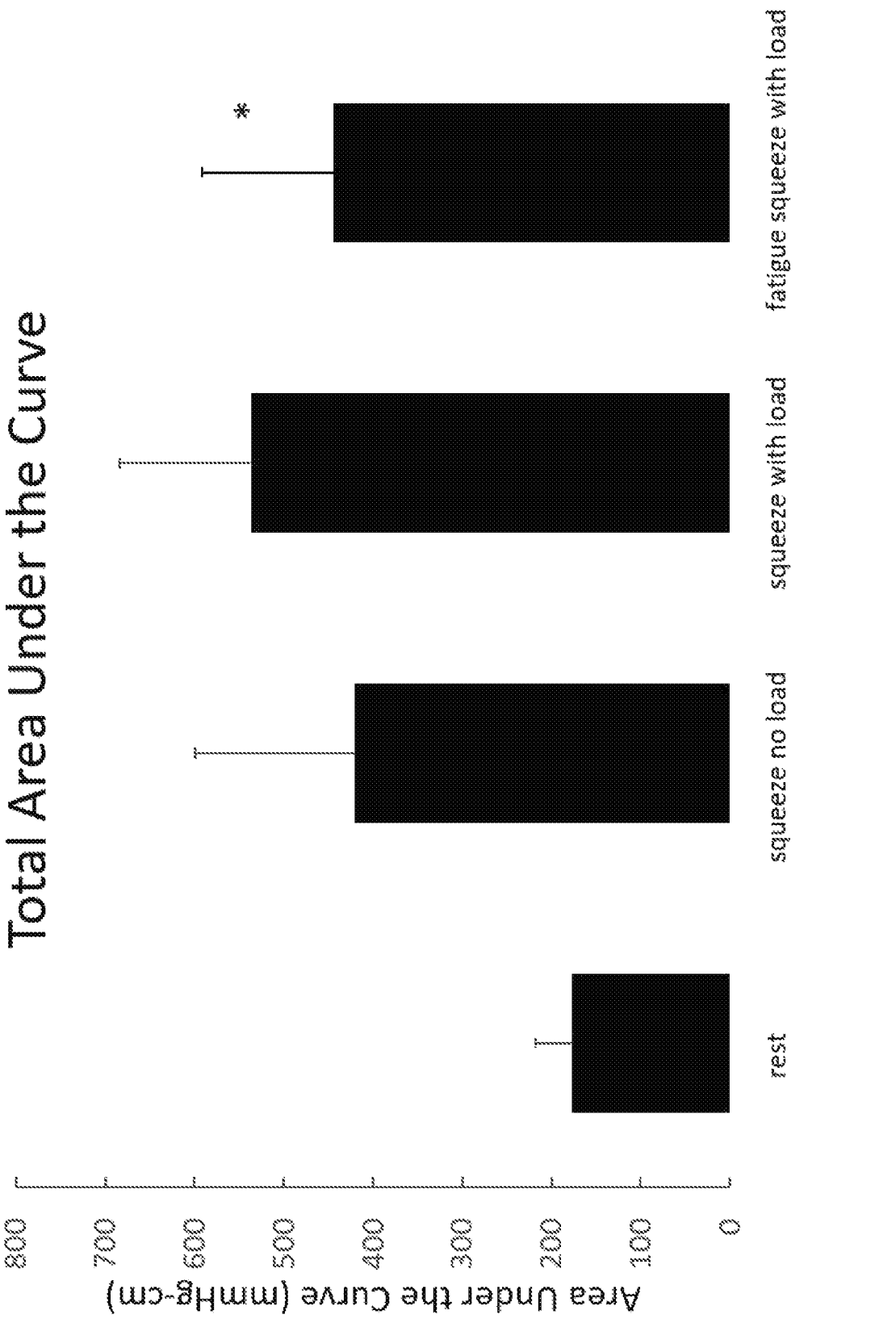

FIG. 14 is a bar graph of the area under the curve in mmHg-cm for differing conditions.

Figure 15:
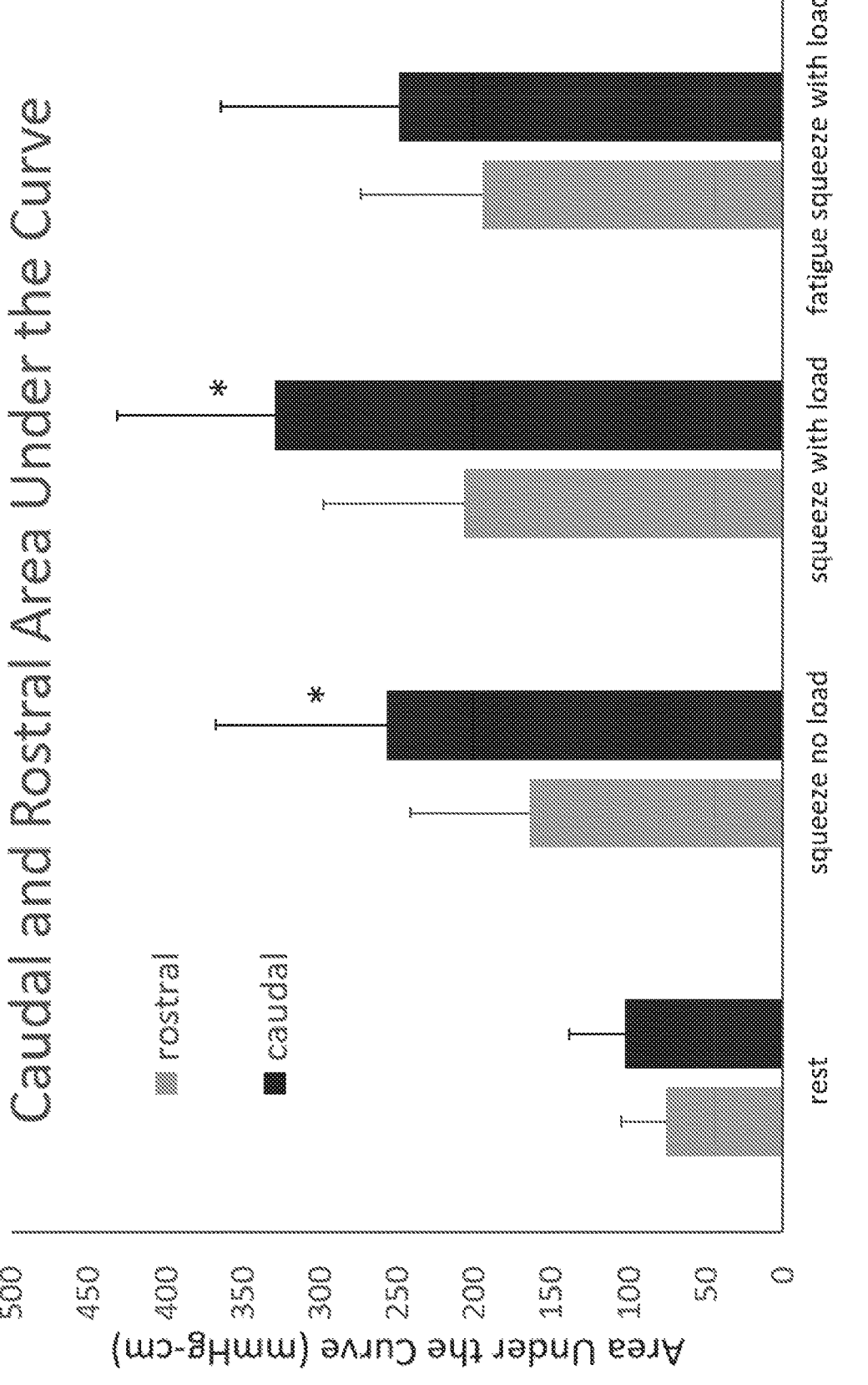

FIG. 15 is another bar graph of the area under the curve in mmHg-cm for differing conditions, and specifically comparing the rostral and caudal locations of the anal canal.

Like reference numerals will be used to refer to like parts from Figure to Figure in the following description of the drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the use the phraseology and terminology used herein is for the purpose of description and should not be regarded as limiting. Furthermore, the use of "right", "left", "front", "back", "upper", "lower", "above", "below", "top", or "bottom" and variations thereof herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Also, it is to be understood that the use the phraseology and terminology used herein is for the purpose of description and should not be regarded as limiting. Furthermore, the use of "right", "left", "front", "back", "upper", "lower", "above", "below", "top", or "bottom" and variations thereof herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

In some embodiments, aspects of the present disclosure, including computerized implementations of methods, can be implemented as a system, method, apparatus, or article of manufacture using standard programming or engineering techniques to produce software, firmware, hardware, or any combination thereof to control a processor device, a computer (e.g., a processor device operatively coupled to a memory), or another electronically operated controller to implement aspects detailed herein. Accordingly, for example, embodiments of the invention can be implemented as a set of instructions, tangibly embodied on a non-transitory computer-readable media, such that a processor device can implement the instructions based upon reading the instructions from the computer-readable media. Some embodiments of the invention can include (or utilize) a device such as an automation device, a special purpose or general purpose computer including various computer hardware, software, firmware, and so on, consistent with the discussion below.

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally, it should be appreciated that a carrier wave can be employed to carry computer-readable electronic data such as those used in transmitting and receiving electronic mail or in accessing a network such as the Internet or a local area network (LAN). Those skilled in the art will recognize many modifications may be made to these configurations without departing from the scope or spirit of the claimed subject matter.

Certain operations of methods according to the invention, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular embodiments of the invention. Further, in some embodiments, certain operations can be executed in parallel, including by dedicated parallel processing devices, or separate computing devices configured to interoperate as part of a large system.

As used herein in the context of computer implementation, unless otherwise specified or limited, the terms "component," "system," "module," etc. are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

As used herein, the term, "controller" and "processor" and "computer" include any device capable of executing a computer program, or any device that includes logic gates configured to execute the described functionality. For example, this may include a processor, a microcontroller, a field-programmable gate array, a programmable logic controller, etc. As another example, these terms may include one or more processors and memories and/or one or more programmable hardware elements, such as any of types of processors, CPUs, microcontrollers, digital signal processors, or other devices capable of executing software instructions.

Unless otherwise specified or limited, phrases similar to "at least one of A, B, and C," "one or more of A, B, and C," and the like, are meant to indicate A, or B, or C, or any combination of A, B, and/or C, including combinations with multiple or single instances of A, B, and/or C.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. Skilled artisans will recognize the examples provided herein have many useful alternatives and fall within the scope of embodiments of the invention.

As described above, surgical approaches intended to treat fecal incontinence have been generally unsuccessful. Additionally, other conventional approaches have attempted to solve this problem, but these too have been largely unsuccessful. For example, one such conventional approach is biofeedback, which aims to educate patients to better understand which muscle of interest (e.g., the anal sphincter) they are flexing. In some cases, the biofeedback approach places electrodes near the muscle of interest, and when the patient flexes the muscle of interest, a visual representation, such as on a display, visually presents a visual image of the electrical firing of the muscle of interest (e.g., similar to electromyography). Although these biofeedback approaches appeared to be promising, they have been unsuccessful, at least because biofeedback does not address the fundamental problem—the strength of the anal sphincter (e.g., the external anal sphincter, or in some cases the internal anal sphincter) does not become improve (e.g., increase in strength, maximum contraction strength, prolonged contraction state, mass of muscle, etc.). In other words, the biofeedback approach (to treat fecal incontinence) is flawed in that it does not use a load against the sphincter muscles, and thus a strengthening effect (if any) on the continence muscles is limited and unpredictable. Additionally, the biofeedback approach typically can only be performed in a physician's office (e.g., the installation of the electrodes, requiring other equipment, etc.).

Some embodiments of the disclosure provide improvements over conventional systems above, and others, for improving fecal incontinence. For example, according to some embodiments, a device is provided that allows individuals to continually overload (or load) the targeted muscles (e.g., continence muscles) in order to strengthen these targeted muscles. Additionally, according to some embodiments, what can also be desired is a device that allows feedback to the individual about the contraction force, its magnitude, and relation to current training. These desired functionalities are largely unavailable. Thus, according to some embodiments, the present disclosure provides a device that includes a miniature anal balloon that can be placed in a transsphincteric region of the subject, so as to load the transsphincteric muscles. The individual contracts/ squeezes any of the transsphincteric muscles, which can be similar to the contraction of the muscles responsible for stopping the flow of urine (i.e., micturition). A tube of a certain length (e.g., twelve inches) can be connected to the transsphincteric balloon, and to a distensible balloon with various markings (indicia) on it. The transsphincteric balloon is filled with a fluid (e.g., air) and sealed accordingly, as to prevent the fluid from escaping. The transsphincteric balloon can then be inserted into the anal canal. Subsequently, the individual can contract the transsphincteric muscles, which can displace a portion of the fluid from the transsphincteric balloon, and into the distensible balloon. Inflation of the distensible balloon, increases the size of the distensible balloon and thus increases the spacing between the markings on the distensible balloon. The increase in the spacing between the markings can not only indicate that a contraction of the transsphincteric muscles has occurred, but it also can indicate the contraction force of the transsphincteric muscles to the individual.

In some embodiments, the transsphincteric balloon can be placed in the vaginal canal (herein, the "vaginal balloon") in order to also load the transsphincteric muscles. Thus, the previous and following description of the transsphincteric balloon can also be applied to the vaginal balloon.

In some embodiments, all of the components of this device can be portable and disposable. For example, after the device is placed in the subject's anus, the device can be thrown away. In some embodiments, the system can be easily portable (e.g., capable of being placed into a bag, suitcase, backpack, etc.). In other embodiments, all components of this device can be cleaned and disinfected for multiple uses. For example, after the device is placed in the subject's anus, the device can be washed, defected, or autoclaved, in order to remove contaminants or possible pathogens from the system, and allow the device to be reused again.

Figure 1:
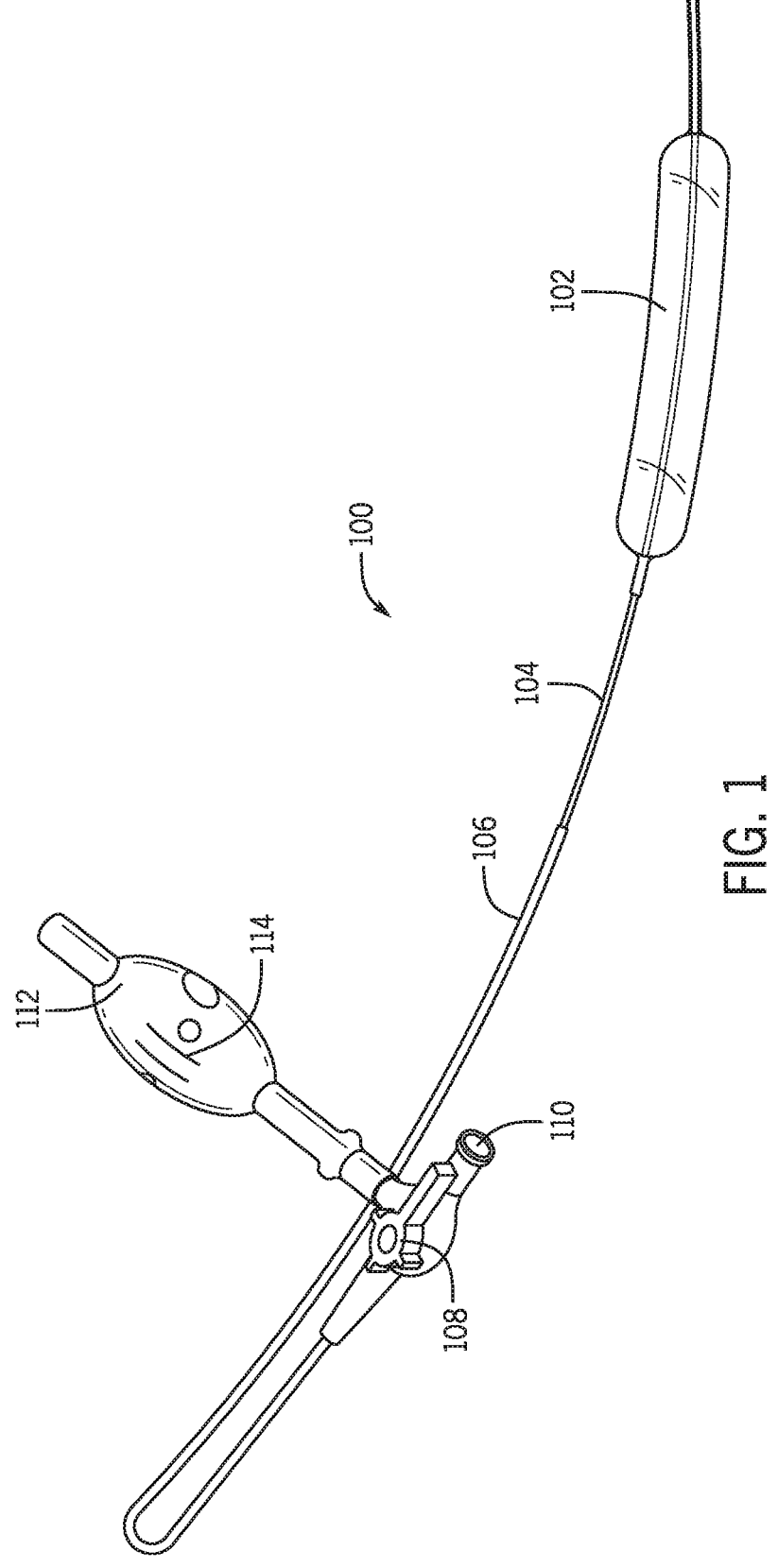
FIG. 1 is a perspective view of a transsphincteric system, according to aspects of the present disclosure.
Figure 2:
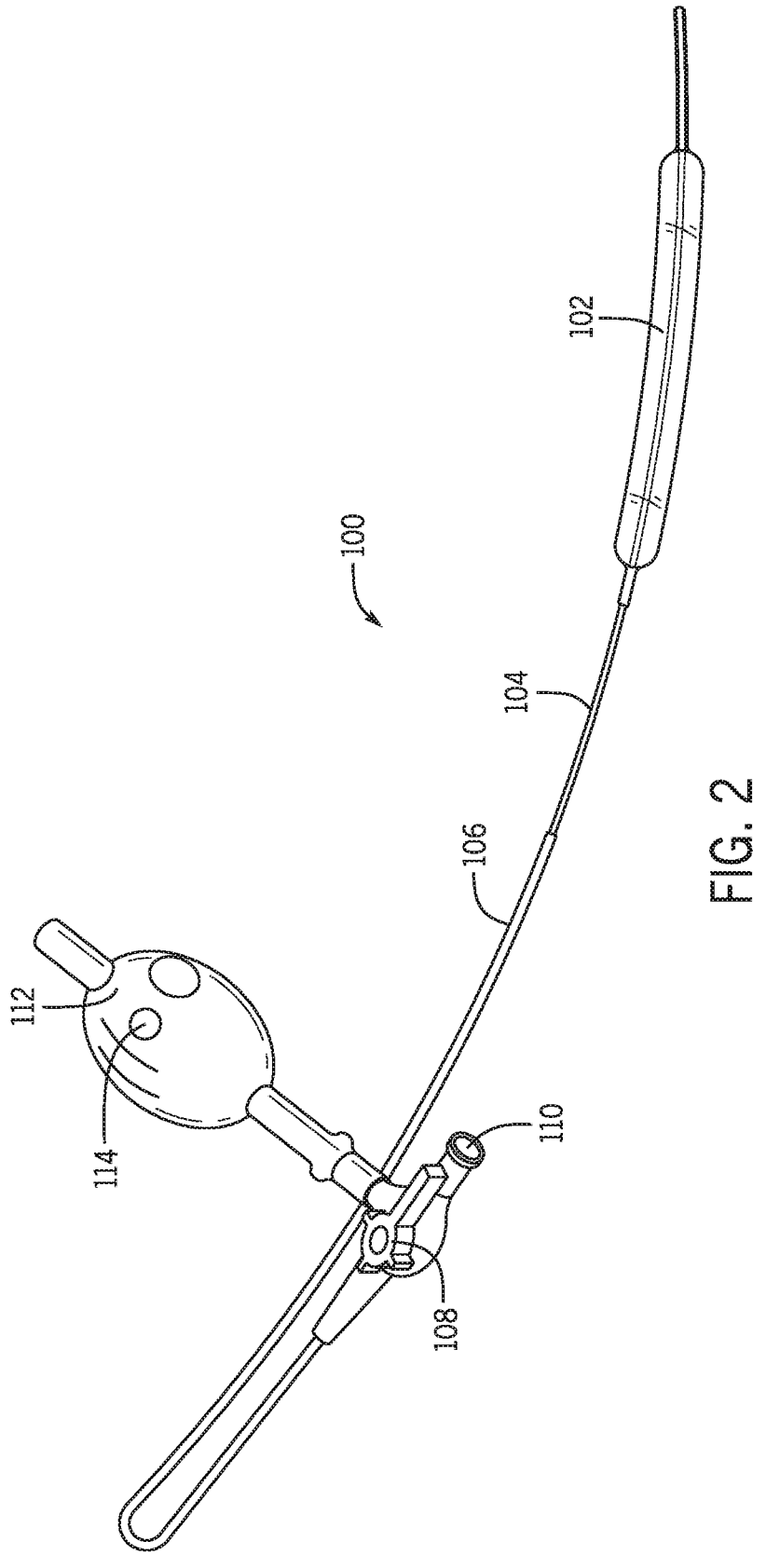
FIG. 2 is another perspective view of the transsphincteric system of FIG. 1 with the transsphincteric balloon being subjected to a first level of compressive force.
Figure 3:
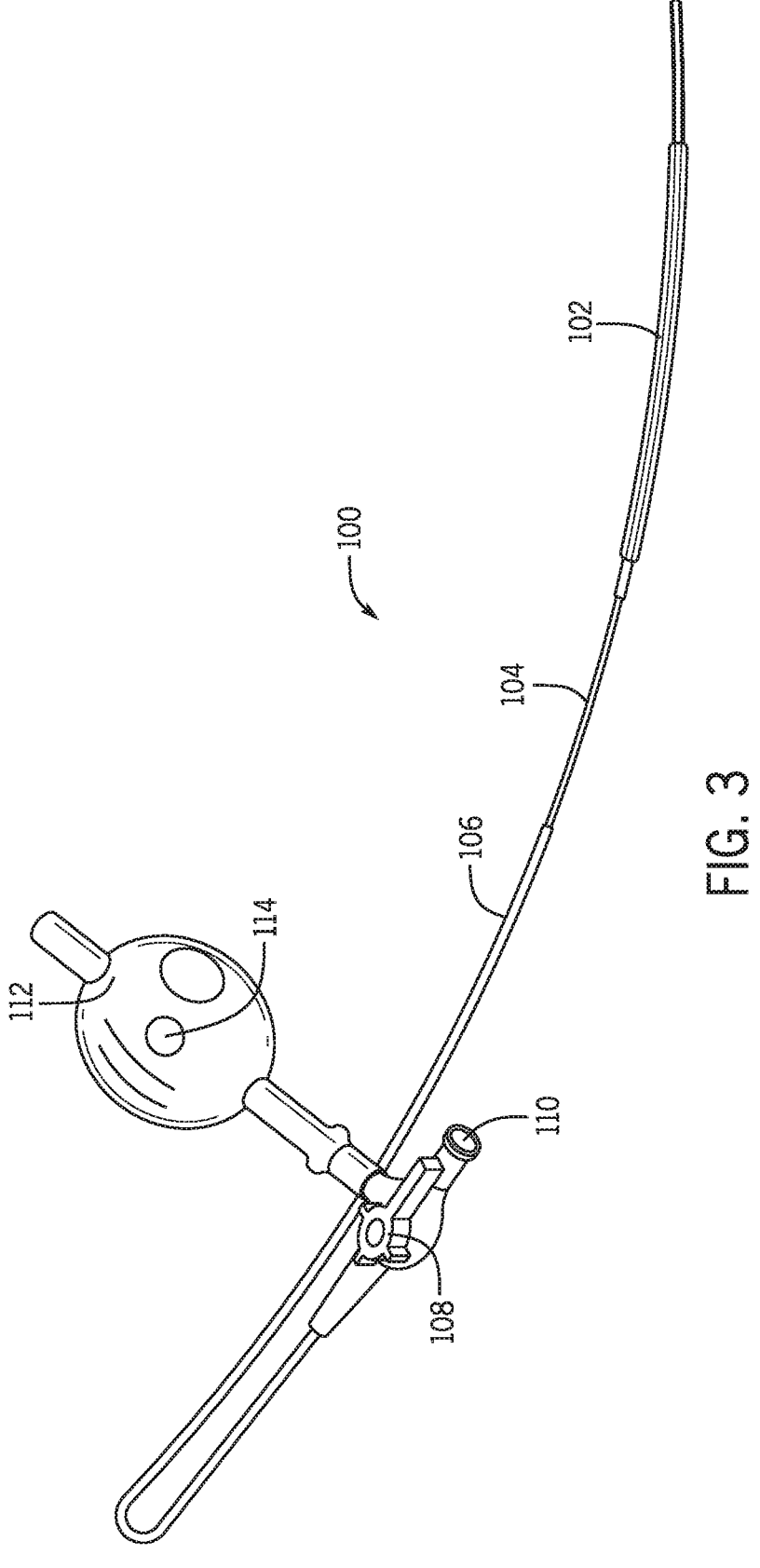
FIG. 3 is yet another perspective view of the transsphincteric system of FIG. 1 with the transsphincteric balloon being subjected to a second level of compressive force.

In the non-limiting embodiment shown in FIGS. 1-3, the transsphincteric system 100 includes a transsphincteric balloon 102, a coupling 104, a fluid conduit 106, a valve 108, and a distensible balloon 112 with markings 114. The transsphincteric balloon 102 can be formed of deformable material capable of containing a fluid at a specific pressure. For example, the transsphincteric balloon 102 can be formed from an elastic polymeric material (e.g., an elastic material, a polymer, etc.). In some embodiments, the transsphincteric balloon 102 can be rigid at a certain pressure or when containing a specific amount of fluid (e.g., air). For example, the transsphincteric balloon 102 can only hold a certain amount of fluid, where the containment of the fluid provides a maximum pressure of the balloon. The transsphincteric balloon 102 includes a coupling 104 integrally formed within the structure of the transsphincteric balloon 102. The coupling 104 provides a cavity that is in fluid communication with the fluid contained by the transsphincteric balloon 102. The structure of the transsphincteric balloon 102 defines an interior surface, where the interior surface is in contact with the fluid, and the cavity of the coupling 104 is in fluid communication with the interior surface of the transsphincteric balloon 102. In some cases, the coupling 104 has internal threads corresponding to external threads on an external portion of the transsphincteric balloon 102, such that the coupling 104 threadingly engages the transsphincteric balloon 102. Generally, the internal threads of the coupling 104 and the external threads of the transsphincteric balloon 102 prevent leaking of the fluid. In some embodiments, the coupling 104 can be other fastening configurations typically used (e.g., magnetic couplings, adhesives, other removably coupling features, fasteners, etc.).

A fluid conduit 106 is attached (or coupled) to the coupling 104 of the transsphincteric balloon 102. The attachment of the fluid conduit 106 to the coupling 104 provides fluid communication between the interior space of the transsphincteric balloon 102 and the fluid conduit 106. In some embodiments, similar to the engagement between the coupling 104 and the transsphincteric balloon 102, the fluid conduit 106 can be coupled to the coupling 104 via previously discussed fastening configurations (e.g., threaded engagement, magnetic couplings, adhesives, other removably coupling features, fasteners, etc.).

The fluid conduit 106 can be formed of any flexible material (e.g., a polymeric material) such that the fluid conduit can be curved about/with respect to the coupling 104 and the transsphincteric balloon 102. In some embodiments, the fluid conduit 106 can have particular interior dimensions (e.g., a specific radius). For example, the fluid conduit 106 can have an internal radius corresponding to a specific fluid resistance, where a larger internal radius corresponds to a smaller fluid resistance and a smaller internal radius corresponds to a larger fluid resistance. In other embodiments, there can be a plurality of fluid conduits each having a specific internal radius and each configured to be coupled to the coupling 104, as discussed above. These other fluid conduits function exactly as discussed with regard to the fluid conduit 106. Thus, the description of the fluid conduit 106 also applied to the other fluid conduits. In some cases, these other fluid conduits can be configured to be joined and thus in fluid communication with other distensible balloons.

The valve 108 includes three ports. An end of the fluid conduit 106 opposite the end attached to the coupling 104 is placed in fluid communication with a first port of the valve 108. A second port of the valve 108 is placed in fluid communication with a coupler 110, and the distensible balloon 112 is placed in fluid communication with a third port of the valve 108. The distensible balloon 112 includes markings 114 (or other indicia) on an exterior surface of the dispensable balloon 112. The markings 114 can include any shape, line segments, etc. As shown in FIGS. 1-3, the markings 114 include two parallel lines, a solid circular marking, and a ring-like marking. Each port of the valve 108 (e.g., the first, second, or third port) can be in fluid communication with any of the other ports of the valve 108 via an adjustable valve member of the valve 108. The valve member of the valve 108 can be rotated to prevent fluid from escaping through any combination or individual port of the valve 108 (e.g., the first, second, or third port). For example, the valve member of the valve 108 can be positioned so as to allow fluid from the fluid source to enter the second port of the valve 108 via coupler 110 and flow through the third port of the valve 108 and into the dispensable balloon 112 thereby inflating the dispensable balloon 112. In some embodiments, the fluid source can be various pumps (e.g., an electric air pump), manually pumps (e.g., a rubber bulb with a valve actuator such as that used in a blood pressure monitor), etc.

The valve member of the valve 108 can also be positioned so as to prevent fluid from escaping through the second port of the valve 108 (e.g., out through the coupler 110). In this configuration, fluid communication exists between the two balloons 102, 112. In other words, fluid is prevented from escaping out of the second port of the valve 108, through the coupler 110, and into the atmosphere. Although the valve 108 is shown being implemented as a three-position (or way) valve, in other alternative embodiments, other valves could be used (e.g., one-way valves, where the entire transsphincteric system 100 is disposed of after usage, two-way valves with different threshold pressures required for allowing or preventing flow directions, etc.). For example, in some alternative configurations, the fluid source can cause fluid (from the fluid source) to flow through the valve 108, into the fluid conduit 106, and into transsphincteric balloon 102, thus inflating the transsphincteric balloon 102. In some cases, fluid (from the fluid source) can flow through the third port of the valve 108 and into distensible balloon 112, thus inflating the distensible balloon 112. In some cases, the fluid source may not be needed for the user. For example, the transsphincteric balloon 102 (and the distensible balloon 112) can be prefilled with a specific air pressure. In some configurations, once the transsphincteric balloon 102 and the distensible balloon 112 are at their desired pressure, the valve member of the valve 108 is positioned so as to only allow fluid communication between the first and third ports of the valve 108, thus preventing fluid from escaping through the second port of the valve 108, through the coupler 110, and into the ambient environment.

As shown in FIG. 1, the transsphincteric system 100 illustrates the transsphincteric balloon 102 inflated with fluid (e.g., air) in a fully inflated state (and corresponding pressure). The valve member of the valve 108 is positioned so as to only allow fluid communication between the first port and the third port of the valve 108 (e.g., preventing fluid from flowing out of the third port of the valve 108, through the coupler 110, and into the atmosphere). As shown in FIG. 1, the distensible balloon 112 is in a fully retracted state.

FIG. 2 illustrates the operation of the transsphincteric system 100. In some embodiments, the transsphincteric balloon 102 is compressed, which displaces a portion of the fluid that was previously contained within the transsphincteric balloon 102. The displaced fluid travels within the fluid conduit 106, through the first port of the valve 108, through the third port of the valve 108, and into the distensible balloon 112 (the displaced fluid does not travel through the second port of the valve 108 due to the positioning of the valve member of the valve 108). The displaced fluid expands the distensible balloon 112, and thus expands the spatial relationship between the markings 114. The expansion of the distensible balloon 112 not only indicates that the transsphincteric balloon 102 has been compressed, but also indicates the magnitude of the compressive force subjected to the transsphincteric balloon 102. For example, the compressive force subjected to the transsphincteric balloon 102 is related to the displaced fluid that travels into and expands the distensible balloon 112. Moreover, the expansion of the distensible balloon 112 increases the spatial relationship between the markings 114, and thus indicates the magnitude of the compressive force subjected to the balloon 102. The comparison of FIGS. 1-3 show the difference of the expansion of the distensible balloon 112. For example, the expansion of the balloon 112 and thus the spatial relationship between the markings 114 is largest in FIG. 3, smaller in FIG. 2, and smallest in FIG. 1. Conversely, the transsphincteric balloon 102 is largest in FIG. 1, smaller in FIG. 2, and smallest in FIG. 3. In some embodiments, such as, after completion of a treatment regimen (e.g., an exercise), the positioning of the valve member of the valve 108 can be adjusted to allow fluid trapped within the transsphincteric system 100 to flow out of the second port of the valve 108 through the coupler 110, and into the atmosphere thereby deflating the either or both of the balloons 102, 112.

In some embodiments, other transsphincteric balloons that can contain a greater/lesser amount of fluid or provide a more rigid/less rigid structure compared to the transsphincteric balloon 102 are also possible, according to some embodiments. For example, other transsphincteric balloons that can contain a greater amount of fluid, or that can include a more rigid structure, can be subjected to greater compressive forces. As another example, other transsphincteric balloons that contain a lesser amount of fluid, or that can include a less rigid structure, can be subjected to lesser compressive forces. These other transsphincteric balloons can be substituted with the transsphincteric balloon 102, such that all the other components discussed with regard to the transsphincteric balloon 102 also apply to these other transsphincteric balloons. In some specific embodiments, the rigidity of the transsphincteric balloon 102 can be changed (or adjusted) as treatment progresses. For example, in some cases, at the beginning of treatment the transsphincteric balloon 102 may be formed of a material (e.g., a deformable material, such as a polymer, a plastic, etc.) having a first rigidity. As treatment progresses, such as when the transsphincteric muscles become stronger, the rigidity of the transsphincteric balloon 102 can be increased, such that the transsphincteric balloon 102 has a second rigidity being greater than the first rigidity. In some cases, the adjustment in rigidity can be realized by changing the material properties of the transsphincteric balloon 102, such as a more rigid material (or materials), while in other cases, the adjustment in rigidity can be realized by changing the geometry (e.g., the thickness, the shape, etc.) of the transsphincteric balloon 102. In other configurations, the transsphincteric balloon 102 can be increased from a first pressure to a second pressure (e.g., by increasing the amount of fluid contained within the transsphincteric system 100), such as when treatment progresses (e.g., when the transsphincteric muscles become stronger).

In some embodiments, the shape of the transsphincteric balloon 102 can be contoured to conform to the patient's anatomy. For example, the diameter of the transsphincteric balloon 102 can be increased in size to accommodate an individual that has a lesser muscle tone of the anal canal. In other configurations, the shape of the transsphincteric balloon 102 need not have a uniform diameter, and thus the profile of the transsphincteric balloon 102 can coincide with the profile of the subject's anal canal. In this configuration, for example, the profile of the transsphincteric balloon 102 can contour the subject's anal canal, while providing loading to the anal canal (e.g., the transsphincteric balloon 102 can be slightly larger than the subject's anal canal to provide the loading to the anal canal). In some embodiments, the aim of the transsphincteric balloon 102 is to allow the transsphincteric balloon 102 to engage the anal canal. Thus, the transsphincteric balloon 102 can take on any shape in order to achieve this.

Figure 4:
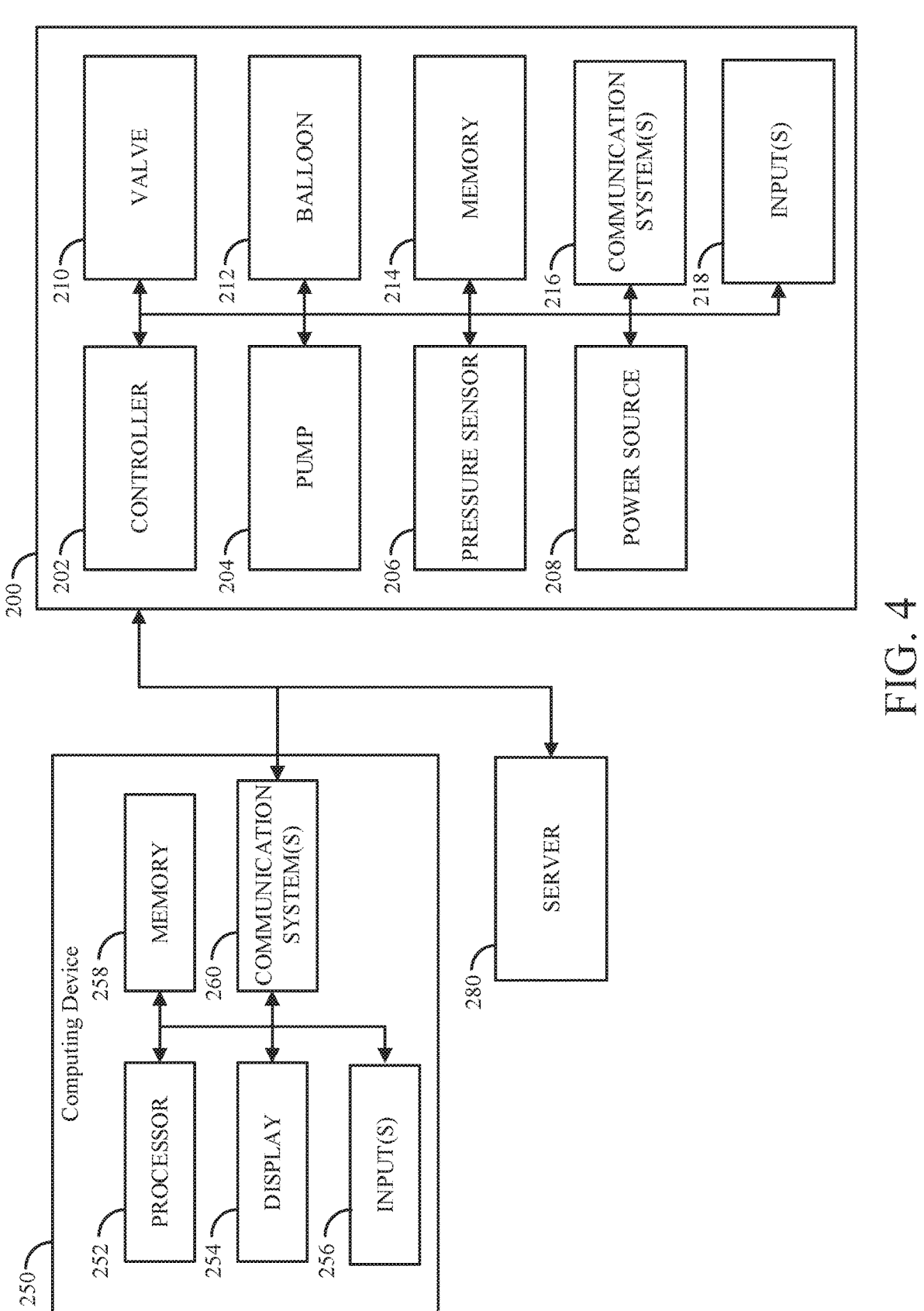
FIG. 4 is a schematic illustration of another transsphincteric system.

FIG. 4 shows a schematic illustration of another embodiment of a transsphincteric system 200 in communication with a computing device 250, and a server 280. The transsphincteric system 200 includes a controller 202, a pump 204, a pressure sensor 206, a power source 208, a valve 210, a transsphincteric balloon 212, memory 214, communication system(s) 216, and input(s) 218. All of the components within the transsphincteric system 200 are in appropriate communication with each other. For example, the transsphincteric balloon 212 is in fluid communication with the valve 210, the pressures sensor 206, and the pump 204. As another example, the controller 202, the pressure sensor 206, the power source 208, the valve 210, memory 214, the communication system 216, and the input 218 are all in communication (e.g., electrical communication, such as wireless, wired, etc.). In some embodiments, inputs 218 can be other sensors, such as a temperature sensor, a humidity sensor, etc.

In some embodiments, the controller 202 includes any suitable hardware or software capable of receiving signals from and controlling the components in communication with the controller 202. For example, in some embodiments, the controller 202 can implement at least a portion of the process (or other functionality) described below, which can, for example be executed from a program (e.g., saved and retrieved from memory 214). The controller 202 can be any suitable hardware processor or combination of processors, such as a central processing unit ("CPU"), a graphics processing unit ("GPU"), etc., which can execute a program, such as including the processes described below.

The pump 204 can embody many different forms as typically used. For example, in some configurations, the pump 204 can be implemented as an electronic pump that is in communication with the controller 202, and is powered by the power source 208. For example, the controller 202 can cause the electronic pump to inflate the transsphincteric balloon 212 with a fluid provided by the electronic pump (e.g., air). In other configurations, the pump 204 can be implemented as a manual pump, such as a manual pump (e.g., a rubber bulb with a valve actuator, such as that used in a blood pressure monitor, etc.).

In some embodiments, the pressure sensor 206 can be any suitable device capable of sensing pressure (or force), such as a pressure transducer, a piezoelectric sensor, a load cell, etc. As will be discussed in more detail below, the pressure sensor 206 is configured to be in fluid communication (and pressure communication) with the internal volume of the transsphincteric balloon 212. This way, the pressure sensor 206 can determine the pressure of the transsphincteric balloon 212, such as used in the processes described below.

The valve 210 can be implemented as a mechanically adjustable valve (e.g., valve 108), or in other configurations, the valve 210 can be implemented as an electrically adjustable valve (e.g., a solenoid valve, a pneumatic valve, etc.). The valve 210 can be positioned along a fluid path spanning between the pump 204, and an interior volume of the transsphincteric balloon 212, and thereby allowing or preventing fluid communication between the pump 204 and the interior volume of the transsphincteric balloon 212.

For example, in some configurations, the controller 202 can cause the valve 210 to allow fluid communication between the pump 204 and the internal volume of the transsphincteric balloon 212. Then, the controller 202 can cause the pump 204 to provide a fluid to the internal volume of the transsphincteric balloon 212 until a pressure (sensed by the pressure sensor 206) meets or exceeds a threshold value. Accordingly, the controller 202 can cause the valve 210 to prevent fluid communication between the pump 204 and the internal volume of the transsphincteric balloon 212. In some configurations, the valve 210 can be implemented as other valves typically used, such as one-way valves, two-way valves, etc., as will be described below.

In some embodiments, the power source 208 can embody many different forms. For example, in some configurations, the power source 208 can be implemented as an electrochemical power source (e.g., a battery, specifically a lithium ion battery), while in other embodiments, the power source 208 can be a wired power source, such as a plug connecting to an electrical outlet, a universal serial bus ("USB") port, etc. In some embodiments, the power source 208 can be a voltage source or a current source, and can sufficiently supply power to the devices within the transsphincteric system 200.

The transsphincteric balloon 212 can be similar to the previously discussed transsphincteric balloon 102. As such, any discussion with respect to the transsphincteric balloon 102 also applies to the transsphincteric balloon 212. The transsphincteric balloon 212 can be formed of a deformable material (with various rigidities) and can be capable of containing various amounts of fluid corresponding to various pressures. In some embodiments, components within the transsphincteric system 200 (e.g., the controller 202, the pressure sensor 206, the power source 208, etc.) can be mounted within the interior volume of the t transssphincteric balloon 212, such as on an interior surface of the balloon. In other configurations, some components within the transsphincteric system 200 can be housed within a housing, external to the transsphincteric balloon 212, as will be discussed below.

In some embodiments, the memory 214 can include any suitable storage device or devices that can be used to store instructions, values, etc., that can be used, for example, by controller 202 (e.g., controller device) to present content using display 254 (e.g., in communication with the transssphincteric system 200, sense pressure values from the pressure sensor 206, etc. Memory 214 can include any suitable volatile memory, non-volatile memory, storage, or any suitable combination thereof. For example, memory 214 can include RAM, ROM, EEPROM, one or more flash drives, one or more hard disks, one or more solid state drives, one or more optical drives, etc. In some embodiments, memory 214 can have encoded thereon a computer program for controlling operation of controller 202 (or computing device 250). In such embodiments, controller 202 can execute at least a portion of the computer program to present content (e.g., user interfaces, images, graphics, tables, reports, etc.), receive information from components within the transsphincteric system 200 (e.g., the pressure sensor 206, etc.), control or cause components within the transsphincteric system 200 to complete a task (e.g., actuate the valve 210, etc.), and transmit information to the computing device 250 and the server 280.

The communication system 216 can include any suitable hardware, firmware, and/or software for communicating with the other systems, over any suitable communication networks. For example, the communication system 216 can include one or more transceivers, one or more communication chips and/or chip sets, etc. In a more particular example, communication system 216 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 216 allows the computing device 250 to communicate with the transssphincteric system 200 (e.g., directly, or indirectly such as via the server 280).

The server 280 can also embody many different forms, as typically used in the art. For example, the server 280 can include processors (e.g., central processing units, graphics processing units, etc.), communication systems (e.g., for communication to other components, and systems such as the internet), etc. The server 280 is shown in FIG. 4 as being in communication with the computing device 250, and the transsphincteric system 200 (e.g., via the communication system 216). In some embodiments, the server 280 can send and receive data among the components in communication, and as such, can instruct (or cause) the computing device 250 and the transsphincteric system 200 to implement specific functionalities (e.g., receive sensor data, store sensor data, transmit sensor data, open a valve, etc.).

As shown in FIG. 4, the computing device 250 can include a processor 252, a display 254, input(s) 256, memory 258, and communication systems 260. In some embodiments, the processor 252 can implement at least a portion of the functionalities, such as the processes described below, which can for example, be executed from a program (e.g., saved and retrieved from memory 258). The processor 252 can be any suitable hardware processor or combination of processors, such as a central processing unit ("CPU"), a graphics processing unit ("GPU"), etc., which can execute a program, which can include the processes described below.

In some embodiments, the display 254 can present a graphical user interface. In some embodiments, the display 254 can include any suitable display devices, such as a computer monitor, a touchscreen, a television, etc. In some embodiments, the inputs 256 can include indicators, sensors, actuatable buttons, a keyboard, a mouse, a graphical user interface, a touchscreen display, and the like. In some embodiments, the inputs 256 allow a user (e.g., a patient, or other practitioner, such as a doctor) to interact with the transsphincteric system 200 (e.g., via a communication network).

The communication system 260 can include any suitable hardware, firmware, and/or software for communicating with the other systems, over any suitable communication networks. For example, the communication system 260 can include one or more transceivers, one or more communication chips and/or chip sets, etc. In a more particular example, communication system 260 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 260 allows the computing device 250 to communicate with the transsphincteric system 200 (e.g., directly, or indirectly such as via a communication network).

In some embodiments, the memory 258 can include any suitable storage device or devices that can be used to store instructions, values, etc., that can be used, for example, by processor 252 to present content using display 254, to communicate with the transsphincteric system 200 via communications system(s) 260, etc. Memory 258 can include any suitable volatile memory, non-volatile memory, storage, or any suitable combination thereof. For example, memory 258 can include RAM, ROM, EEPROM, one or more flash drives, one or more hard disks, one or more solid state drives, one or more optical drives, etc. In some embodiments, memory 258 can have encoded thereon a computer program for controlling operation of the transsphincteric system 200. In such embodiments, processor 252 can execute at least a portion of the computer program to present content (e.g., user interfaces, graphics, tables, reports, etc.), receive content from the transsphincteric system 200, transmit information to the transsphincteric system 200, etc.

As shown in FIG. 4, the computing device 250 is in communication with the transsphincteric system 200 (e.g., via the communication system 216), the computing device is in communication with the server 280, and the server 280 is in communication with the transsphincteric system 200, such that information (or other data) can flow between these components.

In some embodiments, such as after the patient inserts the transsphincteric balloon 212 into the anal canal, the controller 202 is configured to actuate the valve 210, thus allowing fluid to flow from the pump 204 and into the transsphincteric balloon 212. The controller 202 can sense, via the pressure sensor 206, the pressure within the interior region of the transsphincteric balloon 212. Once the interior region of the transsphincteric balloon 212 has reached a certain loading pressure, the controller 202 actuates the valve 210, thus trapping and preventing a further influx (or alternatively, an outflow) of fluid within (or out of) the transsphincteric balloon 212. Once at the certain loading pressure, the transsphincteric balloon 212 can be compressed, and the increase in pressure within the interior region of the transsphincteric balloon 212 is sensed by the controller 202, via the pressure sensor 206. In some embodiments, other loading pressures can be configured. For example, a greater amount of fluid within the interior region of the transsphincteric balloon 212 corresponds to a greater loading pressure, whereas a smaller amount of fluid within the interior region of the transsphincteric balloon 212 corresponds to a smaller loading pressure. In some configurations, such as after the treatment regimen is completed (such as completed for the day), the fluid (e.g., air) trapped within the interior region of the transsphincteric balloon 212 can be released via the valve 210, or the pump 204, where the fluid can escape to the ambient environment (e.g., the atmosphere).

Figure 5:
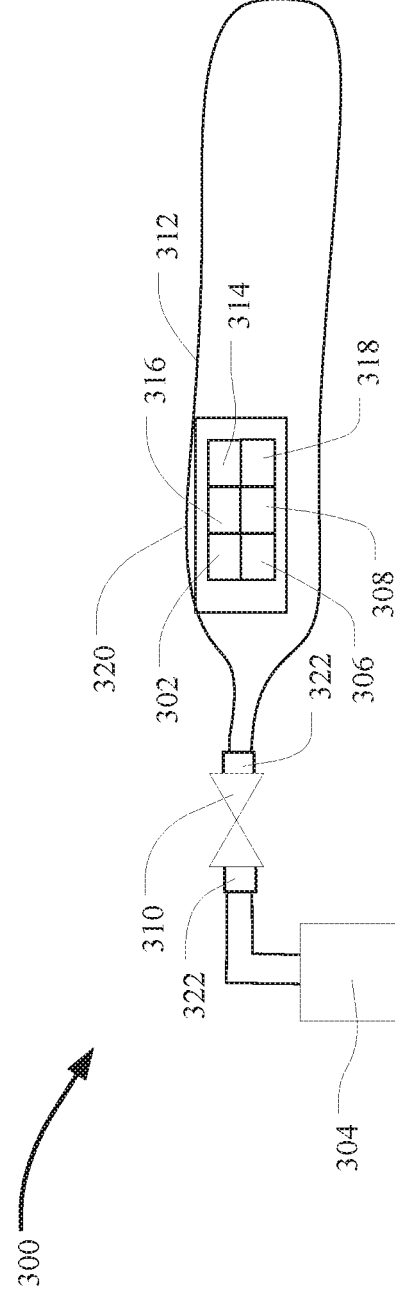
FIG. 5 is an illustration of the transsphincteric system of FIG. 4.

FIG. 5 shows an example of a transsphincteric system 300, which is a specific implementation of the transsphincteric system 200. Thus, the previous description of the transsphincteric system 200 also pertains to the description of the transsphincteric system 300. As shown, the transsphincteric system 300 also includes a controller 302, a pump 304, a pressure sensor 306, a power source 308, a valve 310, a transsphincteric balloon 312, memory 314, communication system(s) 316, and input(s) 318. The transsphincteric system 300 also includes a housing 320, which is configured to retain and secure the controller 302, the pressure sensor 306, the power source 308, the memory 314, the communication system(s) 316, and the inputs 318 within the internal volume of the transsphincteric balloon 312.

In some cases, the housing 320 can include a box, frame, etc., such that the controller 302, the pressure sensor 306, the power source 308, the memory 314, the communication system(s) 316, and the inputs 318 can be coupled (or affixed) to the housing 320 thereby securing these components to the housing 320, and thus relative to the transsphincteric balloon 312, such as when the housing 320 is coupled (or connected) to an interior surface of the transsphincteric balloon 312. In some configurations, the housing 320 can be coupled (or affixed) to the internal surface of the transsphincteric balloon 312. In this configuration, after the transsphincteric system 300 has been used, the entire transsphincteric system 300 except for the valve 310, and the pump 304 can be disposed of accordingly. This may be advantageous, in some cases, where the controller 302, the pressure sensor 306, the power source 308, the memory 314, the communication system(s) 316, and the inputs 318 are relatively inexpensive, such that a consumer (e.g., the patient, practitioner, such as a nurse, technician, doctor, etc.) can readily dispose of the components. In some embodiments, the housing 320 can be removably coupled to the interior of the transsphincteric balloon 312 (e.g., with a hook and loop fastener, magnetically coupled, etc.). In this configuration, such as when the components contained by the housing 320 are relatively expensive, the housing 320 can be retrieved (e.g., by tearing the transsphincteric balloon 312) after the patient has completed the regimen (e.g., the exercise for the day).

In some embodiments, the transsphincteric system 300 also includes couplings 322 that allow some components to be removably coupled from each other. For example, the valve 310 and the transsphincteric balloon 312 can be removably coupled from the pump 304, such as to be discarded. Additionally or alternatively, the transsphincteric balloon 312 can be removably coupled to the valve 310, which can allow the transsphincteric balloon 312 (and corresponding other components) to be disposed, while the valve 310 and the pump 304 remain relatively sterile (e.g., to prevent contamination of feces that can contact the exterior of the transsphincteric balloon 312). The couplings 322 can embody many different forms to removably couple the components, and such that, when the components are coupled fluid communication between components is maintained. For example, the couplings 322 can be threaded engagements, magnetic components, hook and loop fasteners, etc.

Figures 6, 7:
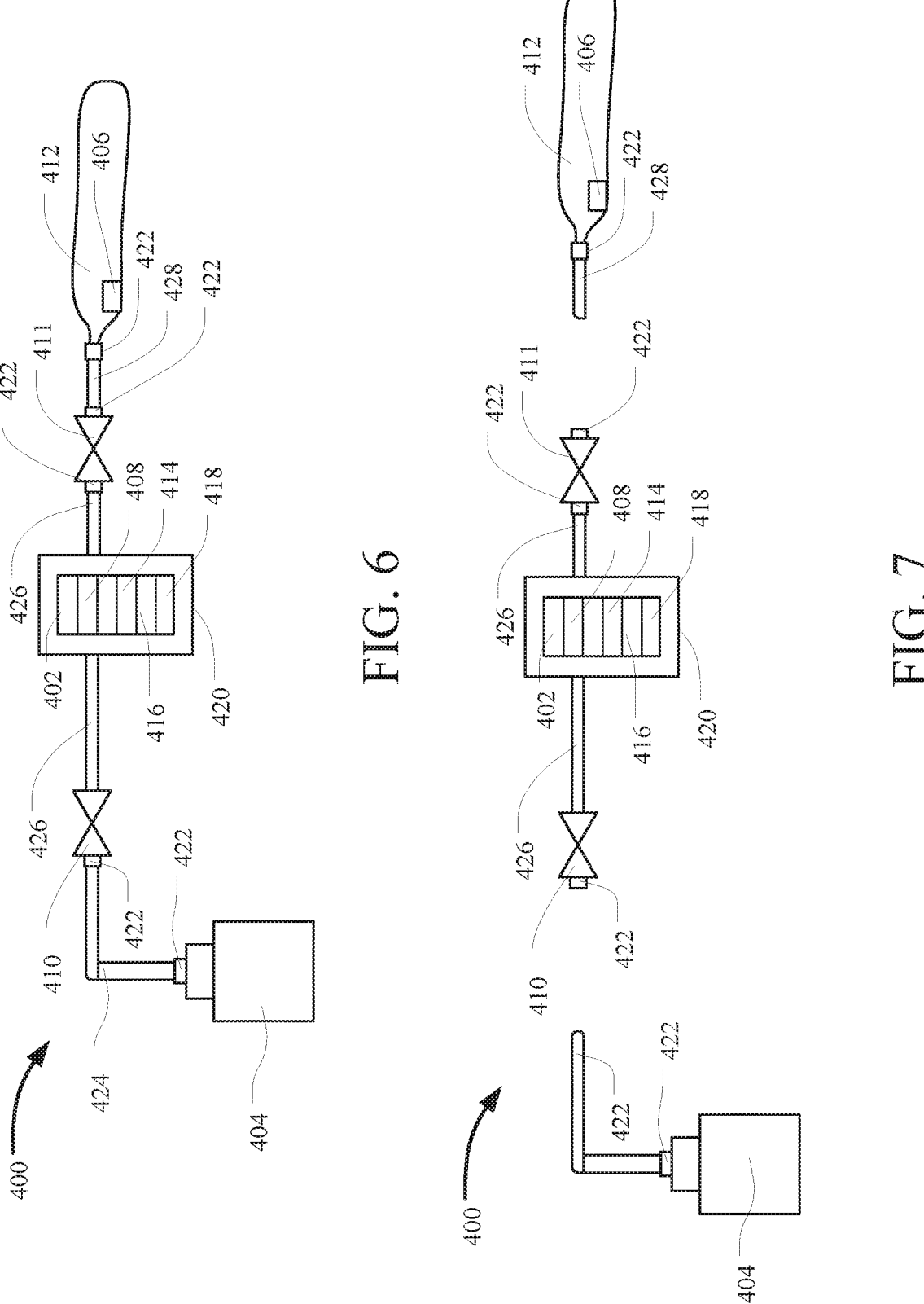
FIG. 6 is another illustration of a transsphincteric system.
FIG. 7 is an illustration of the transsphincteric system of FIG. 6, with groups of components isolated.

FIG. 6 shows an example of a transsphincteric system 400, which is a specific implementation of the transsphincteric system 200. Thus, the previous description of the transsphincteric system 200 also pertains to the description of the transsphincteric system 400. As shown, the transsphincteric system 400 also includes a controller 402, a pump 404, a pressure sensor 406, a power source 408, valves 410, 411, a transsphincteric balloon 412, memory 414, communication system(s) 416, input(s) 418, a housing 420, couplings 422, and conduits 424, 426, 428. As shown, conduit 424 provides fluid communication between the pump 404 (via a coupling) and an end of the valve 410 (via a coupling 422), conduit 426 provides fluid communication between the other end of the valve 410 and an end of the valve 411 (via a coupling 422), and conduit 428 provides fluid communication between the other end of the valve 411 (via a coupling 422) and the internal volume of the transsphincteric balloon 412. The conduit 426 can run through a bore in the housing 420. In some cases, the bore through the housing can have couplings 422 on either end, so as to removably couple the respective conduits to opposing ends of the bore. In some cases, to connect the pressure sensor 406 to the components within the housing 420, leads (or other interfacing electrical conductors) can provide electrical communication between the controller 402 and the pressure sensor 406. As described above, the couplings 422 can embody many different forms to removably couple (e.g., by threaded engagements, magnetic components, hook and loop fasteners, etc.), and correspondingly provide fluid communication, to the components that interface with the particular coupling 422. For example, the conduit 428 can be removably coupled from the valve 411 to provide (or remove) fluid communication between the transsphincteric balloon 412 and the valve 411 via the coupling 422.

FIG. 7 shows an example of the transsphincteric system 400, with groups of components isolated (e.g., by removably coupling components) from each other. For example, as illustrated in FIG. 7, the pump 404, the coupling 422, and the conduit 424 has been removed from the valve 410 at the coupling 422. The valves 410, 411 and components defined between the valves 410, 411, such as the housing 420 (and corresponding components) have been isolated (e.g., not in fluid communication with the other components) by the couplings 422 on respective ends of the valves 410, 411. The transsphincteric balloon 412, the pressure sensor 406, the conduit 428, have been isolated by the coupling 422 on the valve 411. The removably coupled configuration of the transsphincteric system 400 allows a user to readily reuse components within the transsphincteric system 400. For example, in some cases, the transsphincteric balloon 412 (and pressure sensor 406) can simply be discarded after use, whereas the components within the housing 420 can be reused. This way, the components that contact the feces (e.g., the transsphincteric balloon 412) can be discarded, while the other relatively clean components external to the subject (e.g., the housing 420 and corresponding components) are relatively clean and sterile.

In some configurations, the valve 410 can be a one-way valve, such that fluid can only flow from the pump 404, through the conduits 424, 426, 428, and into the transsphincteric balloon 412 thereby inflating the transsphincteric balloon 412. The valve 411 can be an electrically excitable valve (e.g., a solenoid valve) controllable by the controller 402, as described above. In some embodiments, the valve 410 can be a two-way valve, or also an electrically excitable valve, which can allow fluid trapped within the transsphincteric balloon 412 to be vented into the ambient environment to deflate the transsphincteric balloon 412.

Figures 8, 9:
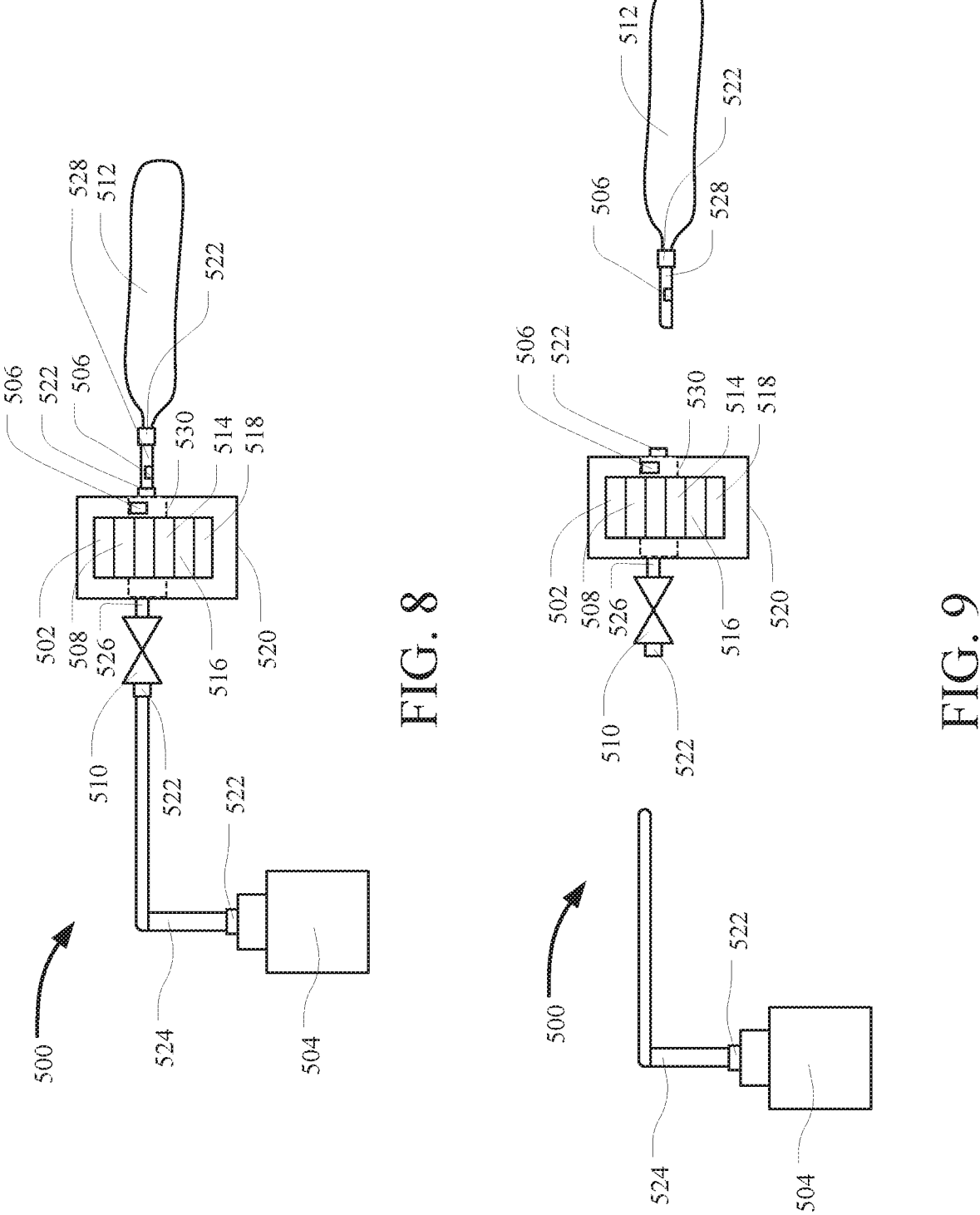
FIG. 8 is an illustration of another transsphincteric system.
FIG. 9 is an illustration of the transsphincteric system of FIG. 8, with groups of components isolated.

FIG. 8 shows an example of a transsphincteric system 500, which is a specific implementation of the transsphincteric system 200. Thus, the previous description of the transsphincteric system 200 also pertains to the description of the transsphincteric system 500. As shown, the transsphincteric system 500 also includes a controller 502, a pump 504, pressure sensors 506, a power source 508, a valve 510, a transsphincteric balloon 512, memory 514, communication system(s) 516, input(s) 518, a housing 520, couplings 522, and conduits 524, 526, 528. As shown, conduit 524 provides fluid communication between the pump 504 (via a coupling) and an end of the valve 510 (via a coupling 522), conduit 526 provides fluid communication between the other end of the valve 510 and a bore 530 through the housing 520, and conduit 528 provides fluid communication between the bore 530 of the housing 520 (via a coupling 522) and the interior volume of the transsphincteric balloon 512 (via a coupling 522).

FIG. 9 shows an example of the transsphincteric system 500, with groups of components isolated (e.g., by removably coupling components) from each other. For example, as illustrated in FIG. 9, the pump 504, the coupling 522, and the conduit 524 has been removed from the valve 510 at the coupling 522. The valve 510, the conduit 526, and the housing 520 (and corresponding components, such as a pressure sensor 506 coupled within the bore 530) have been isolated. The transsphincteric balloon 512, the pressure sensor 506, the conduit 528, have been isolated by the coupling 522 on the housing 520. The removably coupled configuration of the transsphincteric system 500 allows a user to also readily reuse components within the transsphincteric system 500. For example, in some cases, the transsphincteric balloon 512 can simply be discarded after use, whereas the components within the housing 520, such as all of the electrical components including the pressure sensor 506 can be reused. This way, the components that contact the feces (e.g., the transsphincteric balloon 512) can be discarded, or treated to disinfect the transsphincteric balloon 512 (e.g., autoclave, using disinfectant chemicals, etc.), while the other relatively clean components external to the subject (e.g., the housing 520 and corresponding components, such as the electrical components) are relatively clean and sterile. Additionally, this configuration can be advantageous at least because the inexpensive balloon can either be discarded and replaced, or alternatively, because the transsphincteric balloon 512 does not include electrical components (in some configurations), cleaning with harsh chemicals, temperatures, or pressures, does not detrimentally impact the transsphincteric system 500. In some embodiments, the conduit 526 can be omitted, such that the valve 510 is directly in fluid communication (and provides a seal) with the bore 530.

Figure 11:
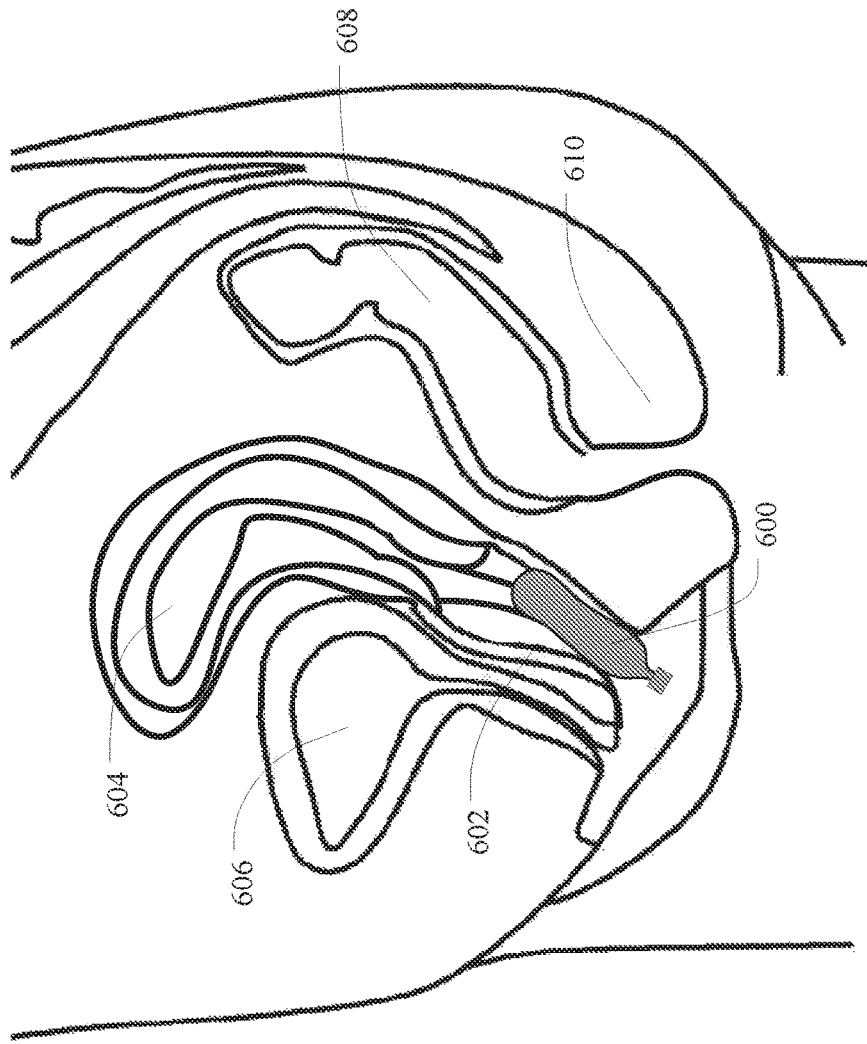
FIG. 11 is a transsphincteric sagittal view of another placement of a transsphincteric system.

FIGS. 10 and 11 show transsphincteric sagittal views of a subject. As illustrated in FIGS. 10 and 11, the subject has a vagina 602, a uterus 604, a bladder 606, a large intestine 608, and a transsphincteric region 610. In some embodiments, fecal incontinence can be caused by weak muscles within the transsphincteric region 610. For example, voluntary muscles within the transsphincteric region 610 can fail to provide the necessary force required to contain feces within the large intestine. Thus, feces leak out of the subject's rectum, where usually the subject is unaware that this is occurring.

As illustrated in FIGS. 10 and 11, in some embodiments, a transsphincteric system 600 can be placed inside subject's anus. The transsphincteric system 600 can be similar to the previously discussed transsphincteric systems. Thus, any discussion with respect to the transsphincteric systems also apply to the transsphincteric system 600. The transsphincteric system 600 can be inserted into the subject's anus in an uninflated state. The transsphincteric system 600 can then be inflated with a certain amount of fluid, or to a desired pressure. In some embodiments, the transsphincteric system 600 can be placed in a subject's anus in an inflated state. The transsphincteric system 600, when inflated, provides a force/pressure (e.g., radial) against the transsphincteric muscles. For example, when the transsphincteric muscles contract, the anal canal also contracts (e.g. radially), towards a medial axis of the subject. Thus, the transsphincteric system 600, when inflated, loads the transsphincteric muscles, expanding the anal canal radially, towards a lateral region of the subject. In some embodiments, the subject contracts the transsphincteric muscles, compressing the transsphincteric system, and overcoming the resistance or loading provided by the transsphincteric system. Overcoming the resistance or loading provided by the transsphincteric system allows the transsphincteric muscles to become stronger, thus preventing fecal incontinence (e.g., once the transsphincteric muscles are strong enough).

In some embodiments, the number of transsphincteric contractions against the transsphincteric system can be a prescribed regiment, based on the transsphincteric muscle characteristics of the subject (e.g., 30 repetitions of contraction twice per day). In some embodiments, after the subject completes a specific regiment (e.g., a first regiment) for a specific duration (e.g., two weeks) the transsphincteric system 600 can increase the amount of fluid or the pressure within the transsphincteric system 600 (e.g., by allowing more fluid within the transsphincteric system 600, or by replacing the transsphincteric balloon with a more rigid one). This increases the loading pressure/force on the transsphincteric muscles, or similarly the force required to contract the transsphincteric muscles. Thus, once a new regiment is completed (e.g., a second regiment), the transsphincteric muscles become even stronger when compared to the transsphincteric muscles after the first regiment. In some embodiments, the progressive increase in loading pressure imparted by the transsphincteric system 600 allows a corresponding increase in strength of the transsphincteric muscles, as the transsphincteric muscles require a larger force to contact (e.g., in order to compress the transsphincteric balloon 600). In some embodiments, as the transsphincteric muscles increase in strength, the intensity of fecal incontinence, or number of fecal incontinence incidents decreases. In some embodiments, once there are no more incidents of fecal incontinence, the prescribed regiments are no longer prescribed.

As discussed above, other fluid conduits such as the fluid conduit 106 each have a specific internal radius that defines a specific fluid resistance. Thus, as the regiment progresses, the subject can replace the coupled fluid conduit (e.g., fluid conduit 106) with another fluid conduit having a smaller internal radius (or longer length), and thus a larger fluid resistance. This increases the force necessary to compress the transsphincteric balloon, allowing the transsphincteric muscles to become stronger. Conversely, the fluid conduit (e.g., fluid conduit 106) can be exchanged for a fluid conduit having a larger internal radius (or shorter length), resulting in a decreased force necessary to compress the transsphincteric balloon. These additional fluid conduits allow the subject to adjust the contraction force of the transsphincteric muscles, without having to replace the transsphincteric balloon.

FIG. 11 illustrates a different placement of the transsphincteric system 600, although any previous description of the transsphincteric system 600 also applies. For example, the transsphincteric system 600 can be placed in the vaginal cavity. In some embodiments, when the transsphincteric system 600 is inflated within the vaginal canal, the transsphincteric muscles are loaded, as previously discussed. In some embodiments, placing the transsphincteric system 600 into the vaginal canal, rather than the anus, in order to load the transsphincteric muscles can be preferable (e.g., more comfortable, etc.).

FIG. 12 illustrates a coronal view of the transsphincteric system 600. In some embodiments, the transsphincteric muscles as previously described, are illustrated in more detail in FIG. 8. The transsphincteric region 610 includes transsphincteric muscles 612. The transsphincteric muscles 612 include smooth muscle 614, and external anal sphincter muscles 616. As previously, discussed above, during the regiment, the external anal sphincter muscles 616 (and in some cases smooth muscle 616) can increase in strength, thus preventing fecal incontinence.

FIG. 13 shows an example of a flowchart of a process 700 for improving fecal incontinence. At least some portions of the process 700 can be implemented on any suitable computing device (e.g., the controller described previously). At 702, process 700 can include determining the desirable treatment regimen, which can include determining the shape, size, etc., of the transsphincteric balloon, the rigidity of the transsphincteric balloon, the fluid pressure (or pressures) of the transsphincteric balloon, the required change in pressure for each repetition, the number of repetitions, the number of repetitions per day for an exercise, the number of exercises per day, the time until the next doctor (or other practitioner) check-up, etc. At 704, process 700 can include selecting the desired transsphincteric balloon, or other parameters (e.g., rigidity, duration of exercise, exercise regimen, etc.).

At 706, process 700 can include completing the exercise regimen, which can include completing an exercise. For example, in some cases, once the treatment regimen has been defined, the user receives the selected balloon, and other parameters, to begin an exercise. At 706, process 700 includes completing the exercise regimen. In some cases, the user can assemble the transsphincteric system prior to beginning the exercise, or the transsphincteric system may be already inflated or installed. The exercise can begin by placing the transsphincteric balloon into the anal cavity of the subject. Then, the transsphincteric balloon is inflated to the previously specified pressure (or simply inserted as in the case of the inflated configuration). In some cases, the controller can actuate a valve to prevent additional fluid (e.g., air from entering the transsphincteric balloon and increasing the pressure), which can happen when a pressure value (e.g., from the pressure sensor) exceeds or meets a threshold value.

Once the transsphincteric balloon is properly placed, the subject voluntarily contracts their anal sphincter. In some cases, the patient may contract their anal sphincter and hold the contraction (e.g., continue squeezing their anal sphincter) for a period of time (e.g., for one second, two seconds, three seconds, four seconds, or until fatigue). In some cases, the transsphincteric system (in according embodiments) transmit pressure data (e.g., pressure values from the pressure sensor, change in pressure of the balloon (e.g., contracting pressure), and when previous pressure data has been acquired, such as previous exercises, the current pressure data can be displayed relative to the previous trials. In some embodiments, the pressure sensed by the pressure sensor must exceed a threshold (e.g., greater than a threshold) to recognize that anal sphincter contraction has occurred. In other cases, the patient can, via a user input, select (e.g., interact with a graphical user interface) that the contraction has initiated so as to instruct the controller to sense a pressure value (or begin data collection from the pressure sensor). In some cases, the patient can also select, via a user input, the rigidity of the transsphincteric balloon (which may be indicated on the transsphincteric balloon itself). This way, the rigidity of the transsphincteric balloon can be calibrated (or otherwise factored) into the calculation of the threshold pressure. For example, if two transsphincteric balloons have the same internal pressure, but one has an increased rigidity, the loading force (such as the force required to contract or otherwise squeeze the anal sphincter) would be increased with increasing rigidity. Thus, in this case, the change in pressure within the transsphincteric balloon does not entirely reflect the rigidity. As such, a multiplier (or other calibration parameter) that reflects the rigidity can be multiplied to the change in pressure within the transsphincteric balloon to more accurately reflect any strength increases in the transsphincteric muscles of the subject.

In some embodiments, the subject can, via a user input, select that the exercise cycle is complete. For example, when the controller (or other suitable computing device) receives the user input, the valves may actuate (or a person can actuate the valve, when the valve is not an electrical valve) to allow fluid within the transsphincteric balloon to vent into the ambient environment thereby deflating the transsphincteric balloon. In some configurations, components within the transsphincteric system can be removably coupled after (or in some configurations before) the transsphincteric balloon has been sufficiently deflated. Then, some components can be discarded (e.g., transsphincteric balloon), thoroughly cleaned (e.g., the transsphincteric balloon), and reused for another usage (e.g., the housing and corresponding components).

At 708 process 700 can determine whether or not the patient has completed the exercise regimen. The exercise regimen can last for any number (or period) of days, weeks, months, years, indefinitely, etc., as appropriately defined previously by the practitioner. In some cases, if the patient has not completed the exercise regimen the process 700 can proceed to 706 to complete the exercise regimen again. If the patient has completed the exercise regimen, the process 700 can proceed to 710 to determine whether or not the patient needs to adjust the regimen.

If the exercise is complete, process 700 can proceed to 710 of process 700. In some cases, the patient can meet with the necessary practitioners to determine if the regimen needs to be adjusted. If the regimen needs to be adjusted, process 700 can proceed back to 702 of process 700 to determine the desirable treatment regimen. Likely, after the patient has completed one exercise regimen, the pressure within the transsphincteric balloon or the rigidity is increased, to increase loading on the transsphincteric muscles (e.g., to require a greater compressive force from the contraction of the transsphincteric balloon), and thereby increase the strength of the transsphincteric muscles over time.

Alternatively, if the regimen does not need to be changed process 700 can proceed to 714 of process 700 to improve fecal incontinence. In some cases, the transsphincteric muscles are of sufficient strength (after increased in strength) where the patient no longer needs to complete the exercise regimen. Alternatively, in some cases, the subject may be required to continue the current exercise regimen (or a modified exercise regimen, such as a decreased loading, number of repetitions, etc., exercise regimen), and thus process 700 can proceed back to 706 to complete the current (or modified regimen).

EXAMPLES

The following examples have been presented in order to further illustrate aspects of the disclosure, and are not meant to limit the scope of the disclosure in any way.

Geometric characteristics of the anal canal high-pressure zone during repetitive contraction against a resistive load can help define the fatigability of muscles involved in fecal continence.

Geometry of the anal canal high pressure zone ("HPZ") reflects the contractile function of various muscles that contribute to fecal continence. Information on the geometry of anal canal HPZ during various contractions such as contraction against a resistive load can potentially be useful in designing strength training exercises for improving fecal incontinence. Aim: (1) To determine and compare the geometry of anal canal HPZ during resting, simple contraction, and contraction against resistive load. (2) To characterize and compare the effect of various contraction modes between rostral and caudal regions of the HPZ. We studied 10 healthy nulliparous female subjects (age 21±3 years). Anal canal pressure was determined by high-resolution anorectal manometry (HRAM, circumferential sensors 1 cm. apart). All subjects performed repetitive contractions (40 consecutive 3 seconds contraction alternating with 3 seconds rest), and this was done with and without an intra-anal compressible resistive load. Averages of 5 squeezes at the start and end of series with and without load were used for analysis. We determined the area under the curve ("AUC") for the squeezes in these conditions. The centroid (center of gravity) was determined using previously described methods. We also compared the caudal and rostral half of the AUC based on the length of anal canal HPZ. Anal canal pressure distribution was defined geometrically by site-wise pressure along the spatial length of the anal canal. AUC was asymmetrical in all conditions and increased significantly during all contractions but decreased during fatigue induced by repetitive contractions against load. (See, FIG. 14, p<0.05). The caudal half of AUC was generally larger than rostral half. This difference reached statistical significance during contractions with and without a load (See, FIG. 15, p=0.01). While the caudal AUC decreased significantly during the last 5 contractions against load, the rostral AUC did not exhibit this finding. Anal canal HPZ geometry displayed as AUC is asymmetrical and represents the contractility of the contributing continence muscles and their anatomic location along the length of the anal canal. Various continence muscles including external anal sphincter components and puborectalis muscles exhibit different fatigability as evidenced by repetitive contraction against load significantly decreasing the total AUC and its caudal half but not rostral half. This finding may reflect the characteristics of the muscles involved in generation of pressure in caudal and distal regions of the anal canal and can guide development of appropriate exercise regimens to improve targeted muscles involved in fecal continence.

FIG. 14 shows a bar graph of the area under the curve in mmHg-cm for differing conditions. The * in FIG. 14 on the fatigue squeeze with load shows a p-value of less than 0.05.

FIG. 15 shows another bar graph of the area under the curve in mmHg-cm for differing conditions, and specifically comparing the rostral and caudal locations of the anal canal. FIG. 15 shows a p-value of 0.01 for the squeeze with no load condition, and the squeeze with load condition.

External Anal Sphincter strength training exercise used a novel continence muscles Resistance Exerciser Device ("cRED") where results showed improved anal sphincter contractility in patients with Fecal Incontinence.

Pelvic floor exercises are frequently used to restore muscle tone and strength in patients with fecal incontinence ("FI"). Development of fatigue during exercise is a prerequisite for successful strength training. Our lab has recently developed a handmade device (continence muscles Resistance Exerciser Device ("cRED")) that provides a predetermined load against external anal sphincter ("EAS") contraction. The example above using this device has confirmed the development of fatigue during repetitive and sustained EAS contraction in healthy nulliparous women. Aim: To evaluate the effect of resistance training using cRED on anal sphincter pressure profile and clinical outcomes in patients with FI. Seven patients (6 female, 72±8 years) with FI were enrolled for a 4 to 6 week exercise protocol. Symptoms were assessed with Vaizey incontinence scores and fecal incontinence quality of life scale ("FIQOL"). High resolution anorectal manometry ("HRAM") was used to evaluate resting pressure, maximum squeeze pressure, and squeeze contractile integral ("CI") of 5 seconds and 20 seconds during sustained squeeze. Patients were instructed to perform 3 sets of 10 repetitive anal sphincter squeezes and 30 second sustained squeezes against cRED twice a day. The cRED is a 6×2.2 cm. intra-anal balloon made of compliant material connected via a 2 mm. diameter tube to an external compliant balloon. The system can be pre-filled with air to different internal pressures using a sphygmomanometer gauge. The two balloons were inflated to apply a pre-determined pressure of 50 mmHg and sealed. Subsequently, any external squeeze applied to the compliant anal balloon displaces air into the compliant external balloon resulting in its increased size which indicates a squeeze has occurred. This air transfer also allows the anal balloon to reduce in diameter yielding to anal contraction allowing isotonic contraction to occur. All patients tolerated the study without any adverse events. Comparison of measured parameters at baseline and end of study showed a significant improvement in maximum squeeze pressure as well as CI of the sustained squeeze during 5 and 20 seconds (Table 1, P=0.02, P=0.003, P=0.005 respectively).

TABLE 1 average resting mean, maximum squeeze pressure, and contractile integral of patients

| Subject Number | Rest mean pre exercise | Rest mean post exercise | Maximum squeeze pre exercise | Maximum squeeze post exercise | CI 5 sec pre exercise | CI 5 sec post exercise | CI 20 sec pre exercise | CI 20 sec post exercise |
|---|---|---|---|---|---|---|---|---|
| 1 | 36 | 26 | 71 | 96 | 267 | 469 | 690 | 1084 |
| 2 | 34 | 54 | 88 | 99 | 279 | 422 | 1036 | 1659 |
| 3 | 15 | 46 | 64 | 80 | 252 | 409 | 885 | 1542 |
| 4 | 22 | 25 | 85 | 78 | 280 | 276 | 737 | 810 |
| 5 | 15 | 16 | 59 | 74 | 183 | 358 | 507 | 1167 |
| 6 | 24 | 21 | 69 | 75 | 453 | 578 | 1682 | 2502 |
| 7 | 0.4 | 8.5 | 52 | 72 | 85 | 166 | 87 | 199 |
| Mean | 20.9 | 28.1 | 69.7 | 82 | 257 | 382.6 | 803 | 1280 |
| SD | 12.2 | 16.3 | 13.1 | 10.9 | 111.5 | 133.4 | 492 | 724 |
| P | 0.23 | | 0.021 | | 0.0029 | | 0.0049 | |

While there was no statistically significant change in resting mean pressure, 4 of 7 subjects showed improvement in resting pressure by at least 10%. Improvement in Vaizey score was reported by 4 of 7 patients, 1 showed no change, and 1 worsened. FIQOL improved in 4 of 7, 2 were unchanged, and 1 worsened. EAS strength training exercise using cRED result in improved anal sphincter contractility in patients with FI. This improvement is associated with clinical improvement in 57% of patients. Further randomized control studies could confirm these findings.

Thus, the invention provides a medical device and a method for reducing incontinence.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The invention claimed is:

1. A medical device for reducing incontinence, the medical device comprising:
a first balloon having a first end and a second end, the first balloon defining an interior surface and an exterior surface, the interior surface defining an interior space, the interior space including a fluid, the first balloon having an outlet disposed on the first end of the balloon, the outlet being in fluid communication with the interior space of the first balloon, wherein the first balloon is dimensioned and configured to be placed in an interior region of a subject's body surrounded by muscle tissue;
a first fluid conduit having a proximal end and a distal end, the proximal end being coupled to the outlet of the first balloon, the fluid conduit being in fluid communication with the outlet and the interior space of the first balloon; and
a pressure sensing detector coupled to the distal end of the first fluid conduit, the pressure sensing detector including a second balloon, the second balloon being in fluid communication with the interior space of the first balloon, the second balloon having an exterior surface with a plurality of markings thereon, wherein the second balloon is configured to be positioned outside of the subject's body, and
wherein compression of the first balloon by contraction of the muscle tissue displaces a portion of the fluid within the interior space of the first balloon, the portion of the fluid moving towards and into the second balloon and causing an increase in interior volume of the second balloon and expansion of the exterior surface of the second balloon, thereby indicating, via the plurality of markings, a contraction force of the muscle tissue and a magnitude of the compression of the first balloon.

2. The medical device of claim 1, wherein the interior region includes a transsphincteric region.

3. The medical device of claim 1, wherein the interior region includes a vaginal cavity.

4. The medical device of claim 1, further comprising:
a second fluid conduit in fluid communication with the interior space of the first balloon, wherein the second fluid conduit defines a fluid path; and
a valve, connectable to a fluid source for supplying the fluid, positioned in the fluid path, wherein the valve allows the fluid to flow into the interior space of the first balloon thereby expanding the first balloon.

5. The medical device of claim 4, wherein the valve allows the fluid within the interior space of the first balloon to flow out of the interior space of the first balloon and be released into the atmosphere.

6. The medical device of claim 5, wherein the fluid within the interior space of the first balloon defines a maximum amount of fluid, such that the first balloon prevents additional fluid from entering the interior space.

7. The medical device of claim 6, wherein the maximum amount of fluid within the interior space of the first balloon defines a first loading pressure.

8. The medical device of claim 7, wherein the first loading pressure compresses the muscle tissue.

* * * * *